US012569266B2

(12) United States Patent
Schings

(10) Patent No.: US 12,569,266 B2
(45) Date of Patent: Mar. 10, 2026

(54) STRAIN AND COMPRESSION FORCE MEASUREMENT FEATURES FOR SURGICAL STAPLER

(71) Applicant: Cilag GmbH International, Zug (CH)

(72) Inventor: Brian D. Schings, Maineville, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/500,297

(22) Filed: Nov. 2, 2023

(65) Prior Publication Data

US 2025/0143733 A1     May 8, 2025

(51) Int. Cl.
| *A61B 17/072* | (2006.01) |
| *A61B 17/00* | (2006.01) |
| *A61B 17/28* | (2006.01) |
| *A61B 90/00* | (2016.01) |

(52) U.S. Cl.
CPC . *A61B 17/2833* (2013.01); *A61B 2017/00115* (2013.01); *A61B 2017/00734* (2013.01); *A61B 2017/07264* (2013.01); *A61B 2017/07271* (2013.01); *A61B 2090/064* (2016.02); *A61B 2090/0811* (2016.02); *A61B 2562/0261* (2013.01)

(58) Field of Classification Search
CPC ...... A61B 2090/064; A61B 2090/0811; A61B 2017/00115; A61B 2017/00734; A61B 2017/07264; A61B 2017/07271; A61B 2562/0261
See application file for complete search history.

(56) References Cited

U.S. PATENT DOCUMENTS

| 7,334,717 | B2 | 2/2008 | Rethy et al. |
| 7,784,663 | B2 * | 8/2010 | Shelton, IV ..... A61B 17/07207 |
| | | | 606/139 |
| 9,724,094 | B2 | 8/2017 | Baber et al. |
| 10,052,044 | B2 | 8/2018 | Shelton, IV et al. |
| 10,357,247 | B2 | 7/2019 | Shelton, IV et al. |
| 10,405,859 | B2 | 9/2019 | Harris et al. |
| 10,631,866 | B2 | 4/2020 | Laurent et al. |
| 10,667,818 | B2 | 6/2020 | McLain et al. |
| 10,687,819 | B2 | 6/2020 | Stokes et al. |
| 10,874,398 | B2 | 12/2020 | Baxter, III et al. |
| 10,898,187 | B2 | 1/2021 | Deck et al. |
| 10,898,197 | B2 | 1/2021 | Baxter, III et al. |

(Continued)

OTHER PUBLICATIONS

U.S. Appl. No. 18/500,305, filed Nov. 2, 2023, by Jaworek et al., entitled: "Clamp Force Sensor for Surgical Stapler."

(Continued)

*Primary Examiner* — Michelle Lopez
(74) *Attorney, Agent, or Firm* — FBT Gibbons LLP

(57) ABSTRACT

An apparatus includes a first and second elongate member that can releasably couple together to in order to cooperate to clamp and staple tissue, a latch member that can latch the first and second elongate member to clamp tissue, a firing assembly that can sever and staple clamped tissue, and a strain measuring assembly associated with the first elongate member. The strain measuring assembly being capable of measuring a strain value on the first elongate member, compare the strain value with a predetermined limit associated with successful staple formation, and generate a signal in response to the comparison.

18 Claims, 27 Drawing Sheets

(56) References Cited

U.S. PATENT DOCUMENTS

| | | | |
|---|---|---|---|
| 10,905,419 | B2 | 2/2021 | Schings et al. |
| 10,932,781 | B2 | 3/2021 | Jones et al. |
| 11,033,266 | B2 | 6/2021 | Jones et al. |
| 11,045,193 | B2 | 6/2021 | Schings et al. |
| 11,071,545 | B2 | 7/2021 | Baber et al. |
| 11,109,866 | B2 | 9/2021 | Shelton, IV et al. |
| 11,219,454 | B2 | 1/2022 | Schings et al. |
| 11,224,425 | B2 | 1/2022 | Schings |
| 11,229,433 | B2 | 1/2022 | Schings et al. |
| 11,278,285 | B2 | 3/2022 | Deck et al. |
| 11,284,894 | B2 * | 3/2022 | Park .................... A61B 17/072 |
| 11,399,827 | B2 | 8/2022 | Schings |
| 11,937,812 | B2 | 3/2024 | Schings et al. |
| 2005/0131390 | A1 | 6/2005 | Heinrich et al. |
| 2006/0273135 | A1 * | 12/2006 | Beetel .................. A61B 17/128 |
| | | | 227/175.1 |
| 2017/0296185 | A1 | 10/2017 | Swensgard et al. |
| 2021/0361376 | A1 | 11/2021 | Eschbach et al. |
| 2022/0008071 | A1 | 1/2022 | Rose et al. |
| 2022/0142641 | A1 | 5/2022 | Wang |
| 2022/0406452 | A1 * | 12/2022 | Shelton, IV ........... A61B 34/37 |
| 2023/0123673 | A1 | 4/2023 | Gonenc et al. |
| 2023/0329704 | A1 | 10/2023 | Hess et al. |
| 2025/0041000 | A1 | 2/2025 | Shelton, IV et al. |

OTHER PUBLICATIONS

U.S. Appl. No. 29/842,580, filed Jun. 14, 2022, by Schings et al., entitled: "Staple Cartridge for a Linear Surgical Stapler."
U.S. Appl. No. 29/842,581, filed Jun. 14, 2022, by Deck et al., entitled: "Linear Surgical Stapler."
Extended European Search Report, received for European Application No. 24209381.3, mailed on Dec. 10, 2024, 8 pages.
Extended European Search Report, received for European Application No. 24209384.7, mailed on Feb. 17, 2025, 8 pages.

* cited by examiner

1200

CLAMP DEVICE ON LOAD CELL
DURING MANUFACTURING          ~1202

MEASURE ANVIL STRAIN WITH STRAIN GUAGE          ~1204

UTILIZED MEASURED ANVIL STRAIN
TO GENERATE UNIQUELY CHARACTERIZED
DEVICE PARAMETER          ~1206

WRITE PARAMETER TO MEMORY ON PCB          ~1208

STRAIN AND COMPRESSION FORCE MEASUREMENT FEATURES FOR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

3

Figure 19:
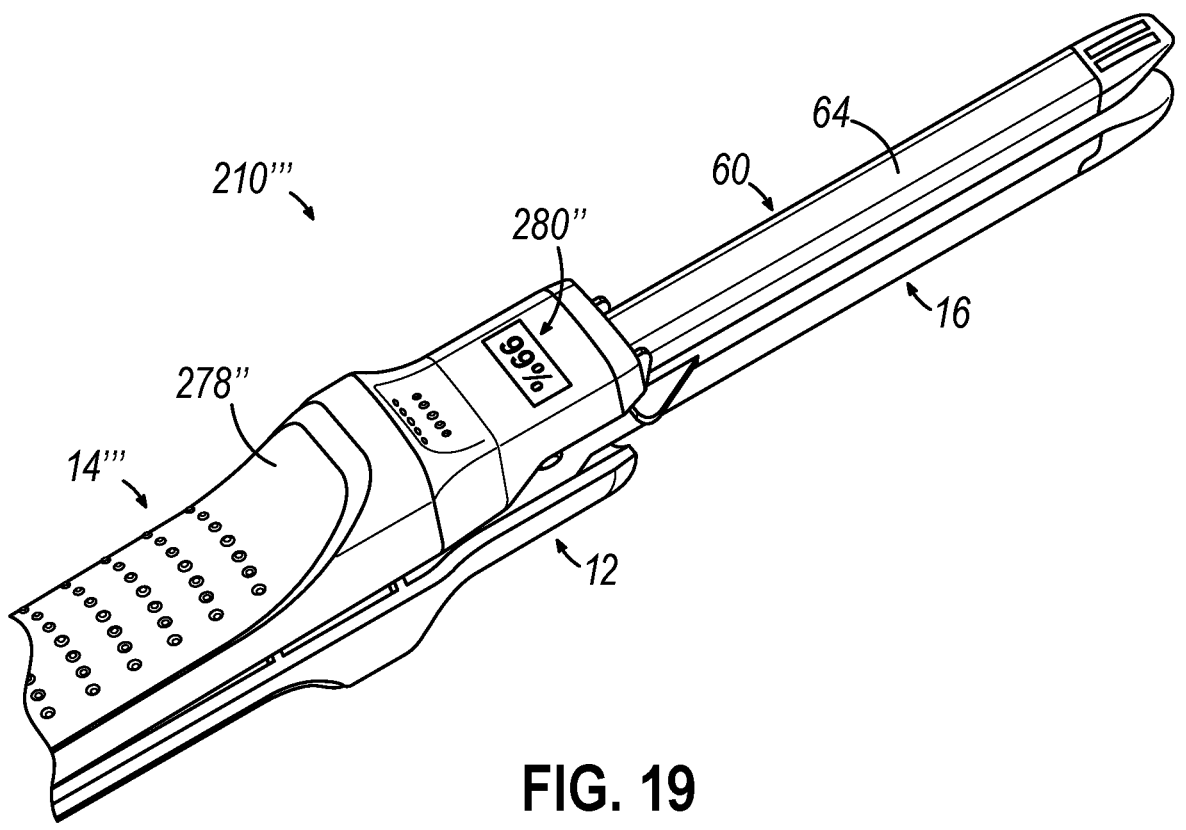
Figure 20:
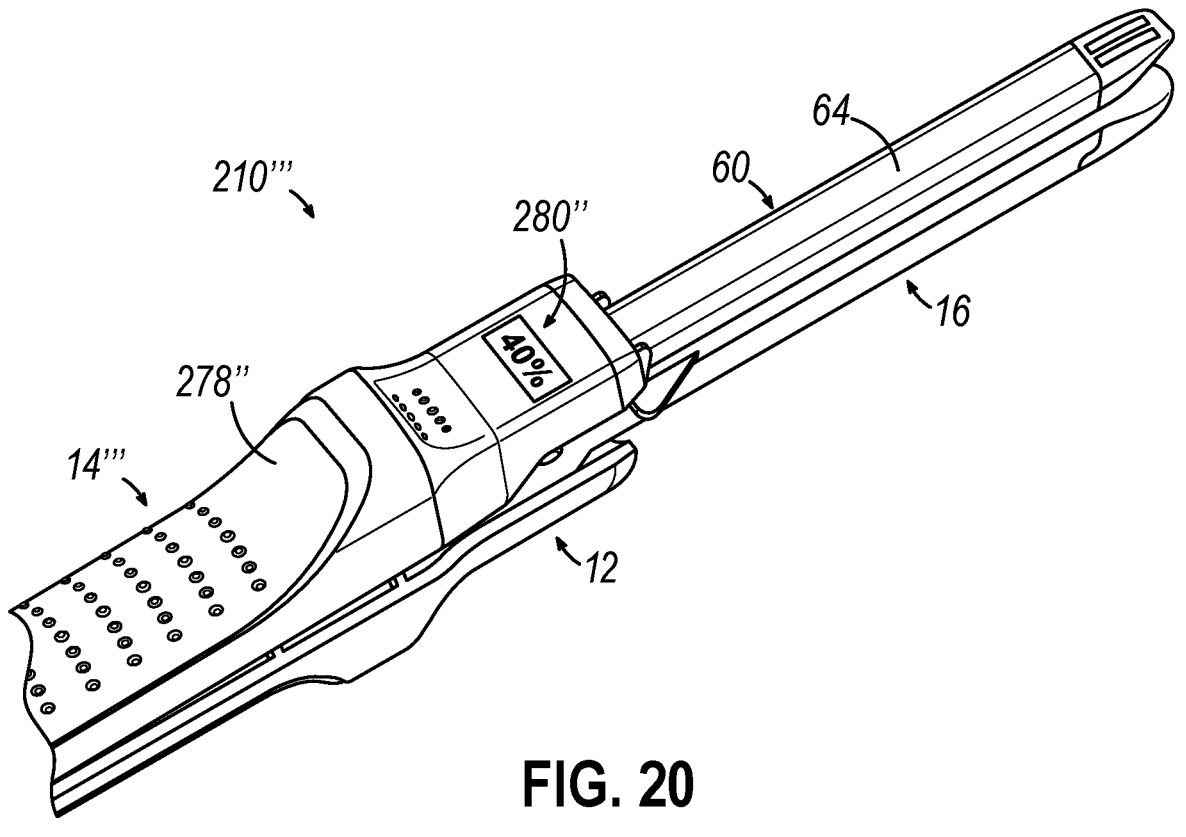
Figure 21:
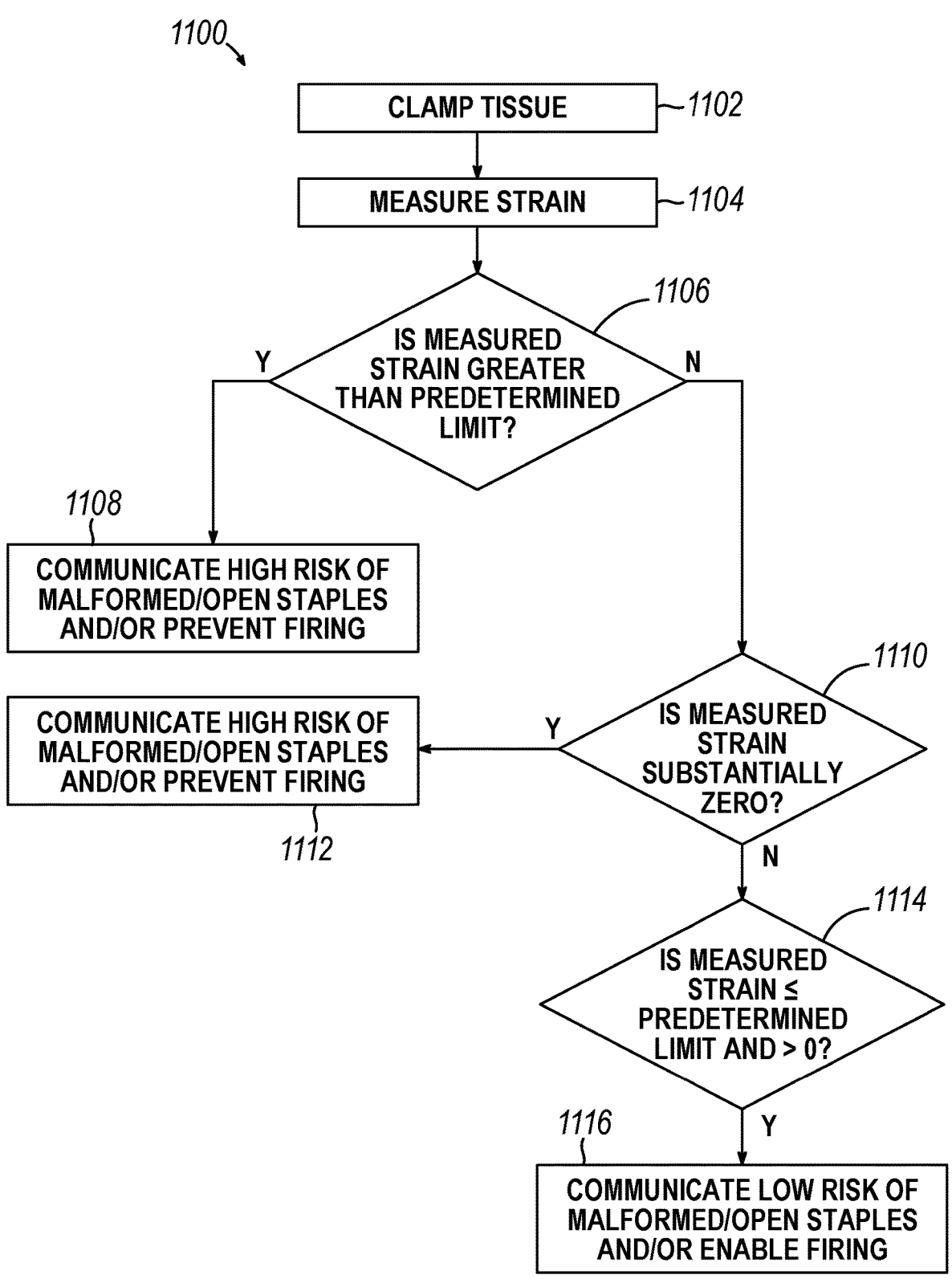
Figure 22:
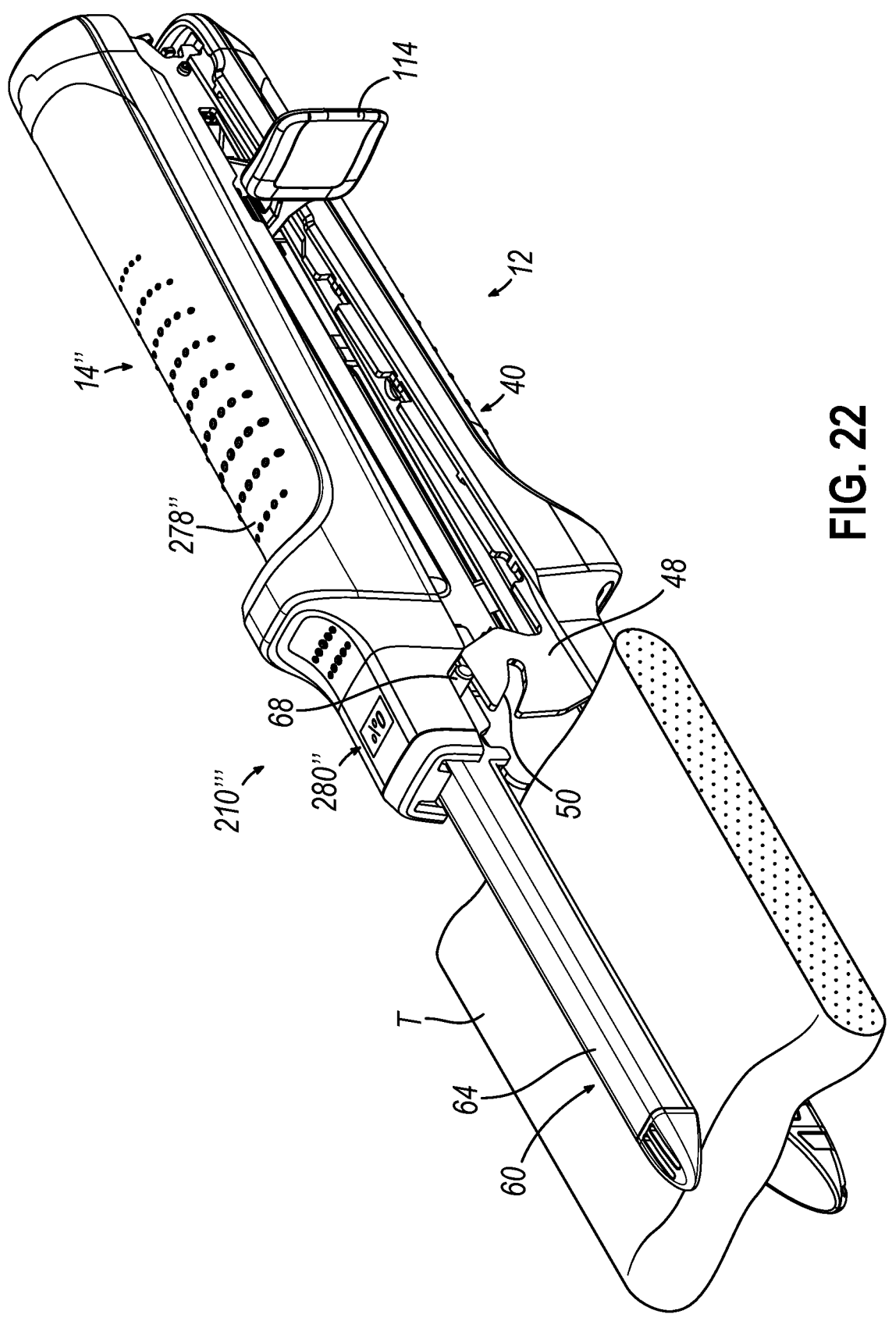
Figure 23:
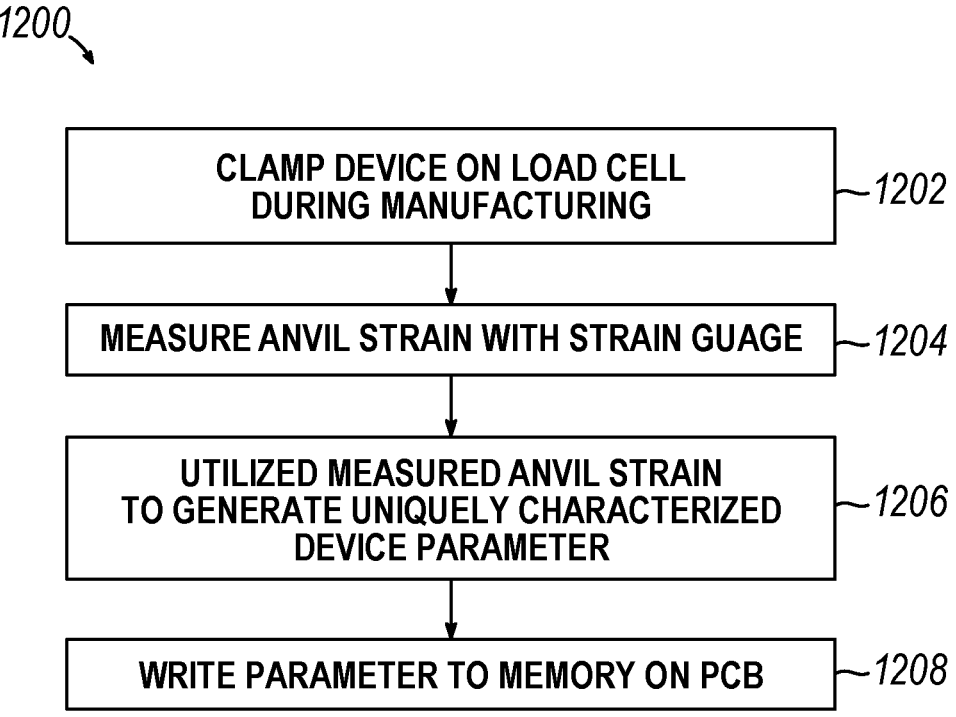
Figure 24A:
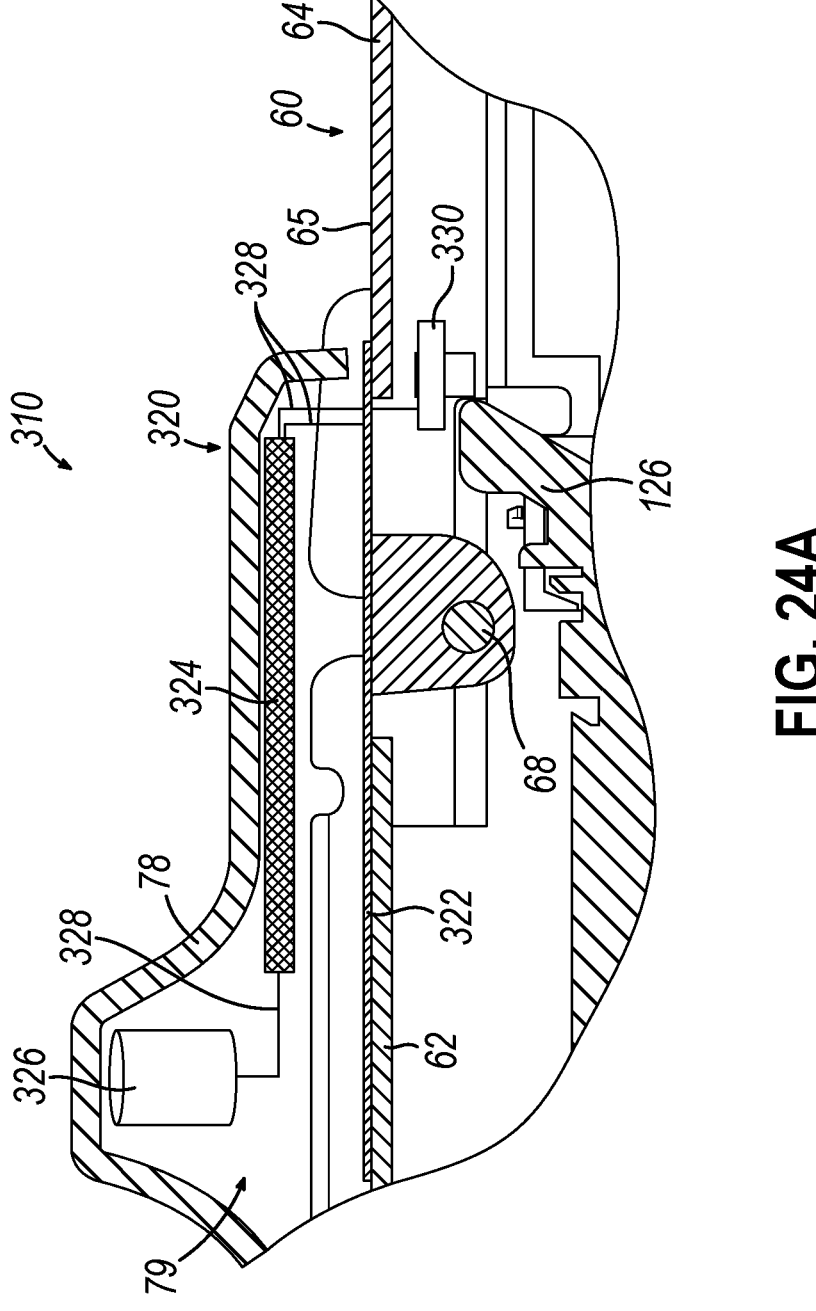
Figure 24B:
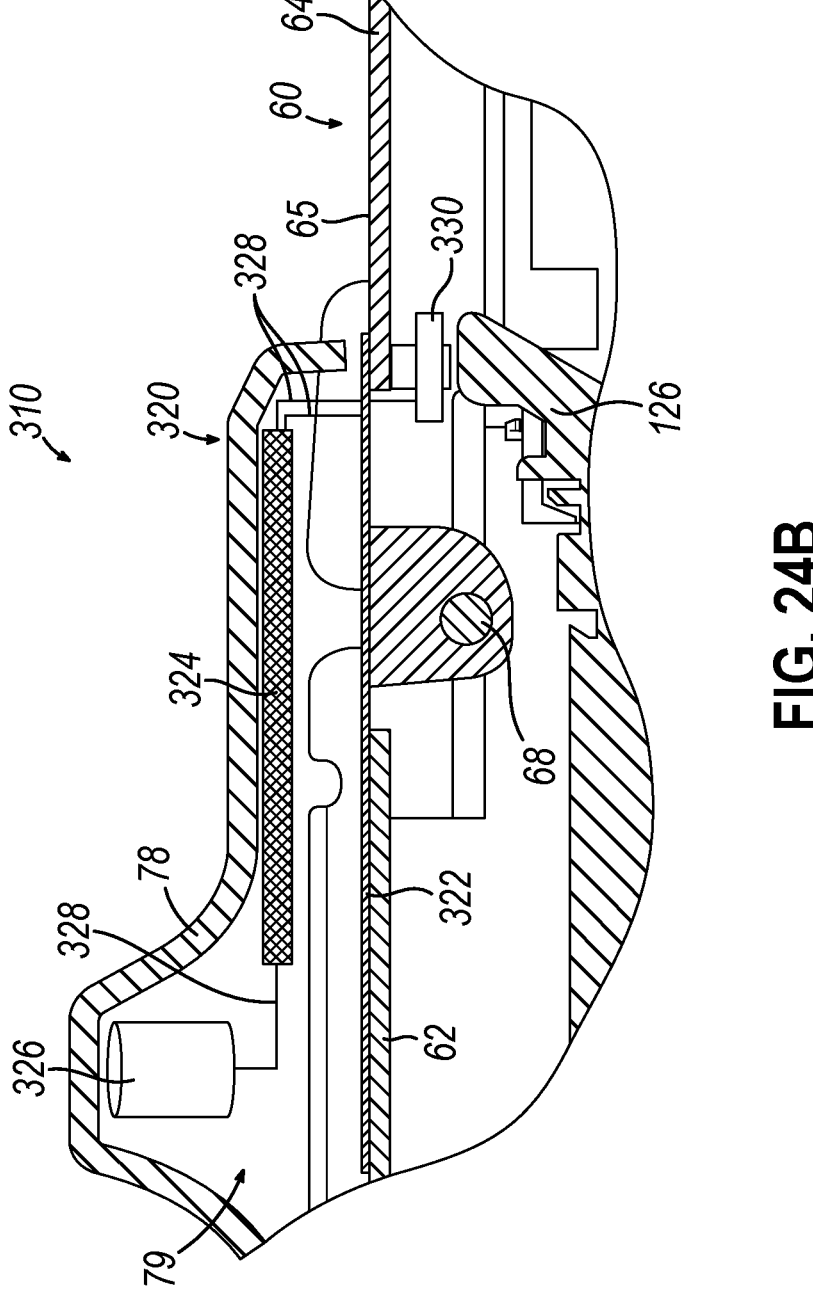
Figure 25:
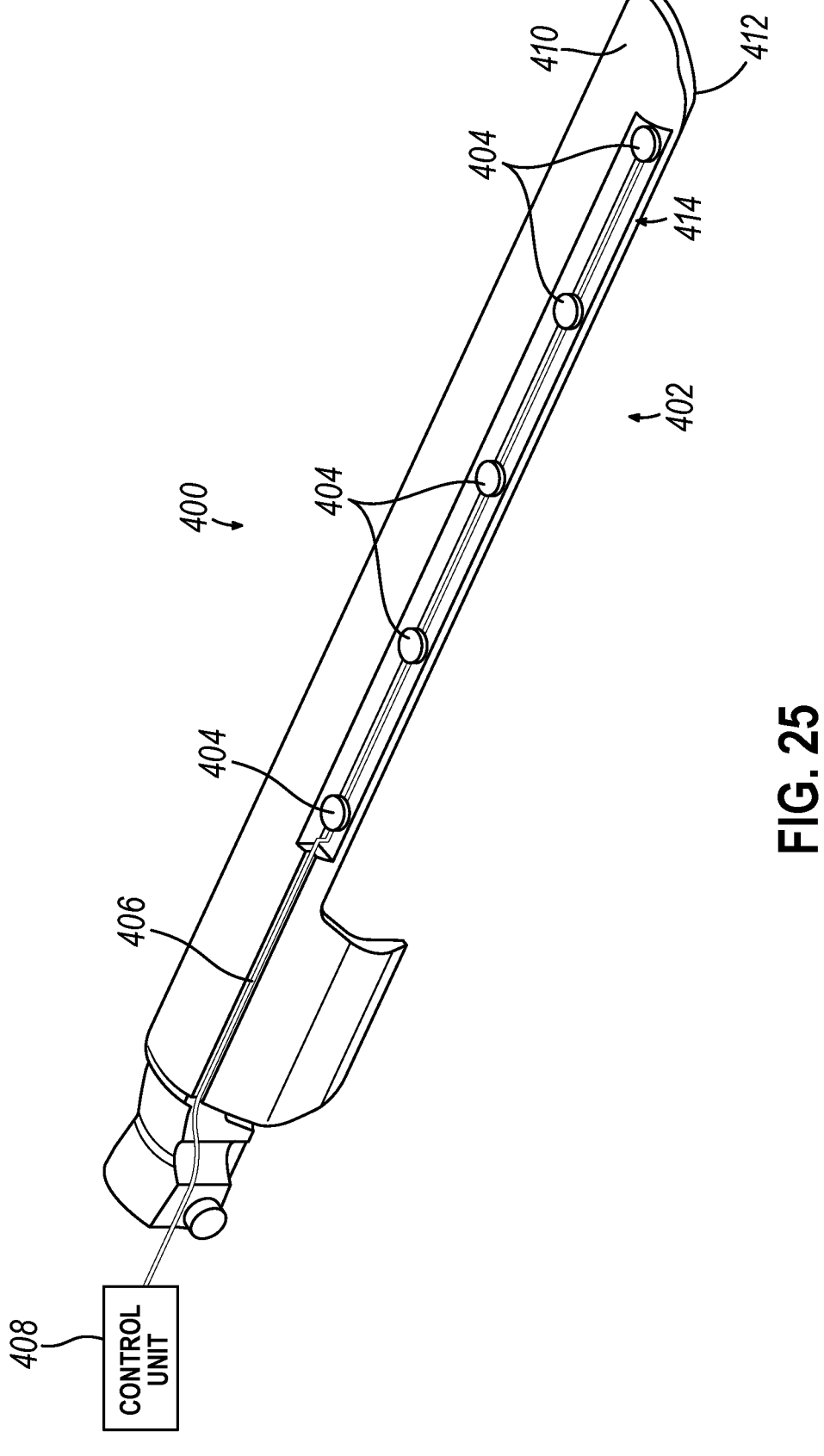
Figure 26:
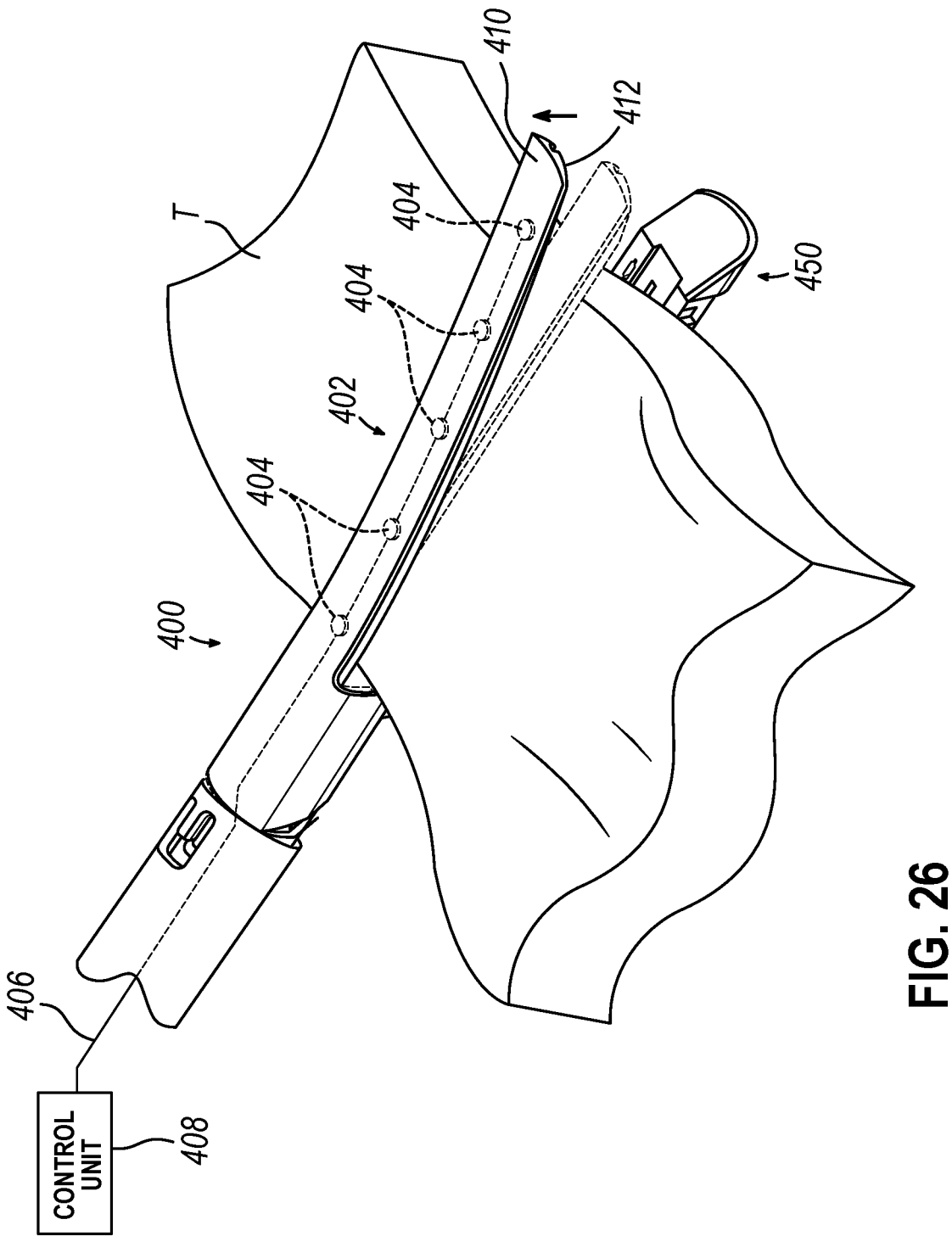

FIG. 19 depicts a perspective view of an alternative linear surgical stapler having a clamp quality indicator indicating distal portions of the stapler halves are properly grasping tissue such that the chances of a quality staple formation are high;

FIG. 20 depicts a perspective view of the linear surgical stapler of FIG. 19, where the clamp quality indicator of FIG. 19 indicates distal portions of the stapler halves are improperly grasping tissue such that the chances of a quality staple formation are low;

FIG. 21 depicts a flowchart of an illustrative method of use of a linear surgical stapler having an anvil strain measuring assembly;

FIG. 22 depicts a perspective view of the linear surgical stapler of FIG. 19, showing closure of a clamp lever while a distal pin of the anvil half is misaligned with clamp lever jaws of the cartridge half, where the clamp quality indicator of FIG. 19 indicates distal portions of the stapler halves are improperly grasping tissue such that the chances of a quality staple formation are substantially zero;

FIG. 23 depicts a flowchart of an example method of calibrating an anvil strain measuring assembly of a linear surgical stapler;

FIG. 24A depicts a cross-sectional view of an alternative linear surgical stapler having an anvil strain measuring assembly with a lockout device, where the lockout device is in the locked configuration;

FIG. 24B depicts a cross-sectional view of an alternative linear surgical stapler having an anvil strain measuring assembly with a lockout device, where the lockout device is in the unlocked configuration;

FIG. 25 depicts a perspective view of a laparoscopic anvil having an anvil strain measuring assembly; and FIG. 26 depicts a perspective view of a laparoscopic end effector having the anvil of FIG. 25, where the end effector is grasping tissue.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms "about" and "approximately" as used herein in connection with any numerical values or ranges indicate a suitable dimensional tolerance that allows the referenced feature(s) to function for its intended purpose as described herein.

I. Illustrative Linear Surgical Staplers

A. Overview of Linear Surgical Stapler

Figure 1:
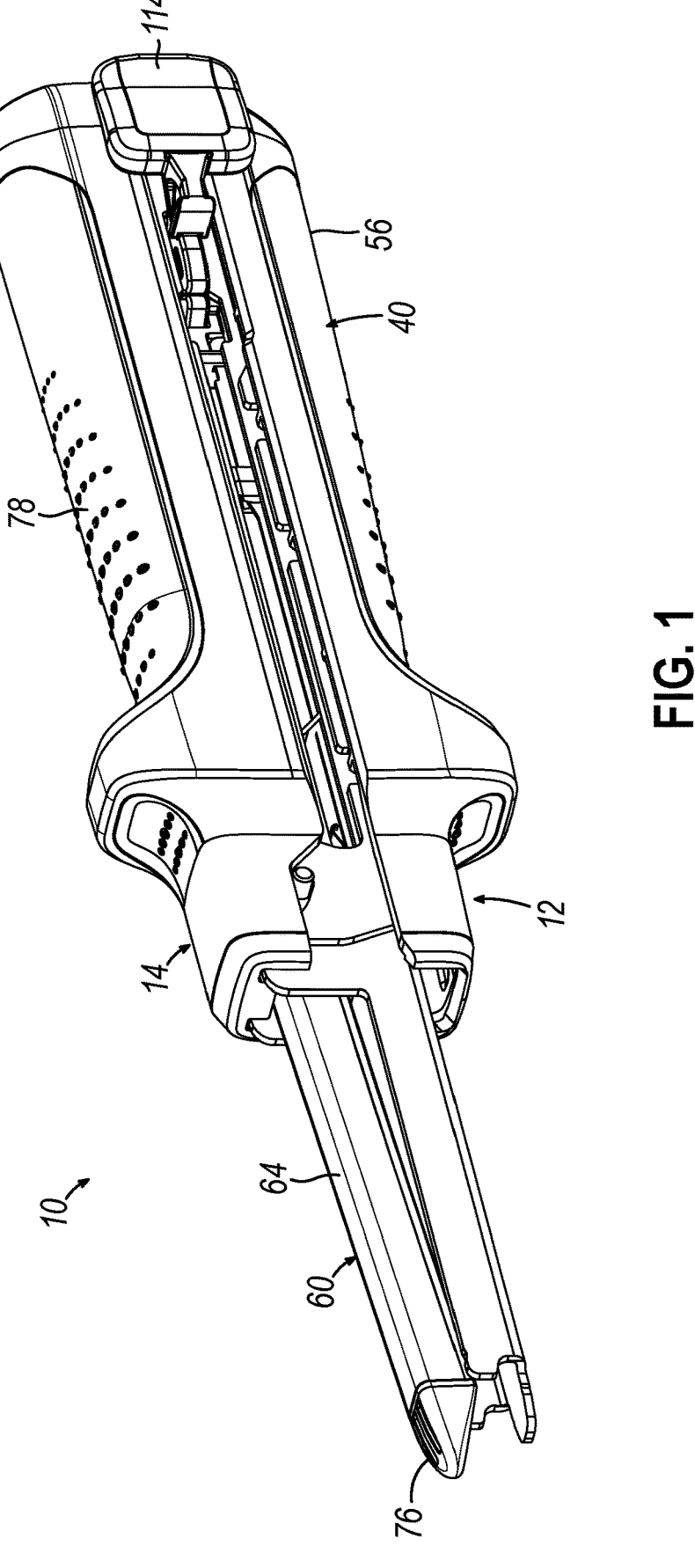
FIG. 1 depicts a perspective view of an illustrative linear surgical stapler, showing a cartridge half and an anvil half of the stapler coupled together with a clamp lever of the cartridge half in a fully closed position.
Figure 2:
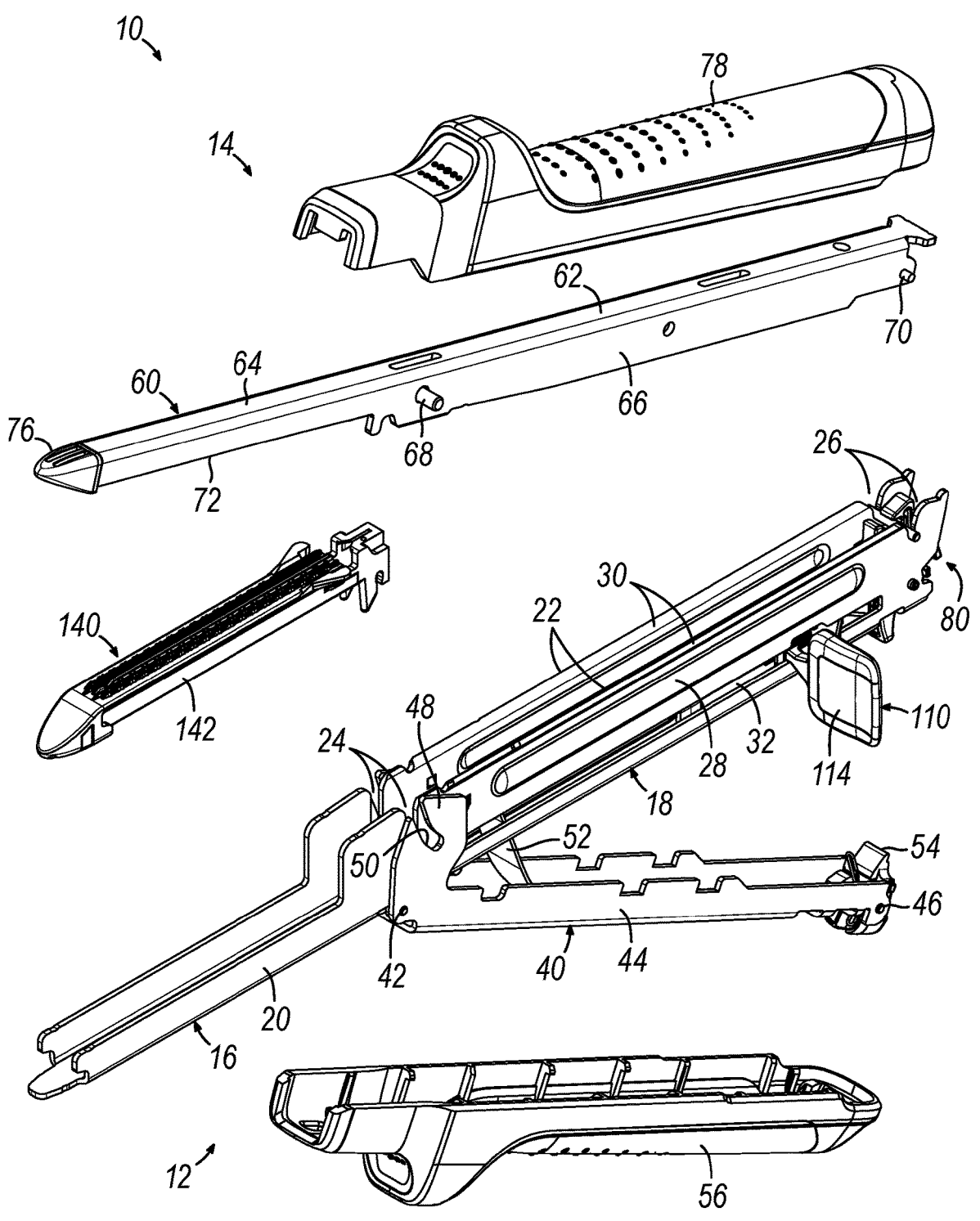
FIG. 2 depicts an exploded perspective view of the linear surgical stapler of FIG. 1, additionally showing a staple cartridge.

FIGS. 1-2 show an illustrative linear surgical stapler (10) (also referred to as a "linear cutter") suitable for use in a variety of cutting and stapling procedures, such as a gastro-intestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes a first elongate body and/or member in the form of an elongate cartridge channel (16) having a proximal frame portion (18) and a distal jaw portion (20). Proximal frame portion (18) slidably retains a firing assembly (110) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Figure 4:
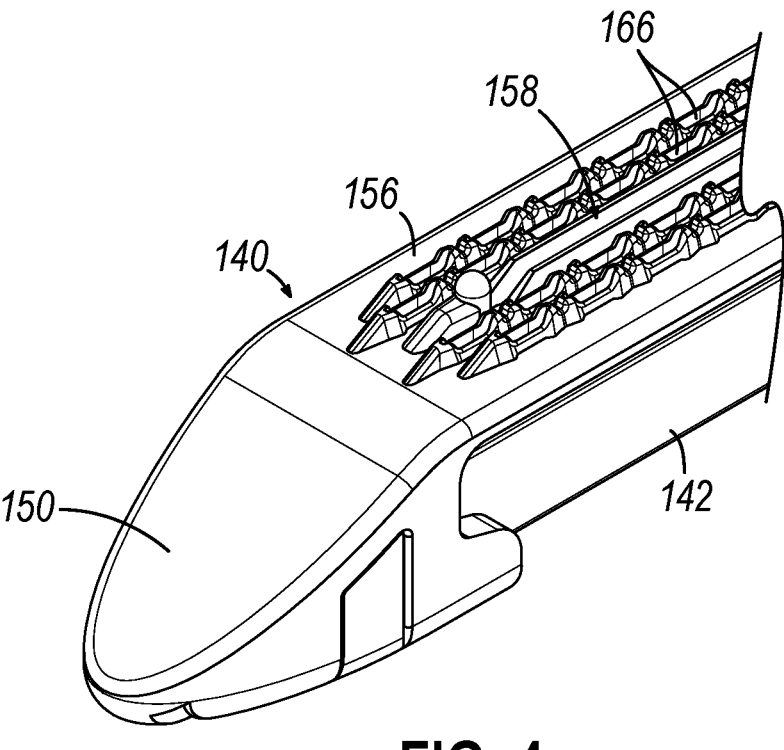
FIG. 4 depicts a perspective view of a distal end portion of the staple cartridge of FIG. 2.

Distal jaw portion (20) of cartridge channel (16) is configured to releasably receive a staple cartridge (140) (or "reload"). As shown in FIG. 4, staple cartridge (140) includes a cartridge body (142) having an upper side that defines a first stapling surface in the form of a deck (156) having a plurality of staple openings (166) that house a plurality of staples and corresponding staple drivers.

Cartridge half (12) further includes a clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 9A:
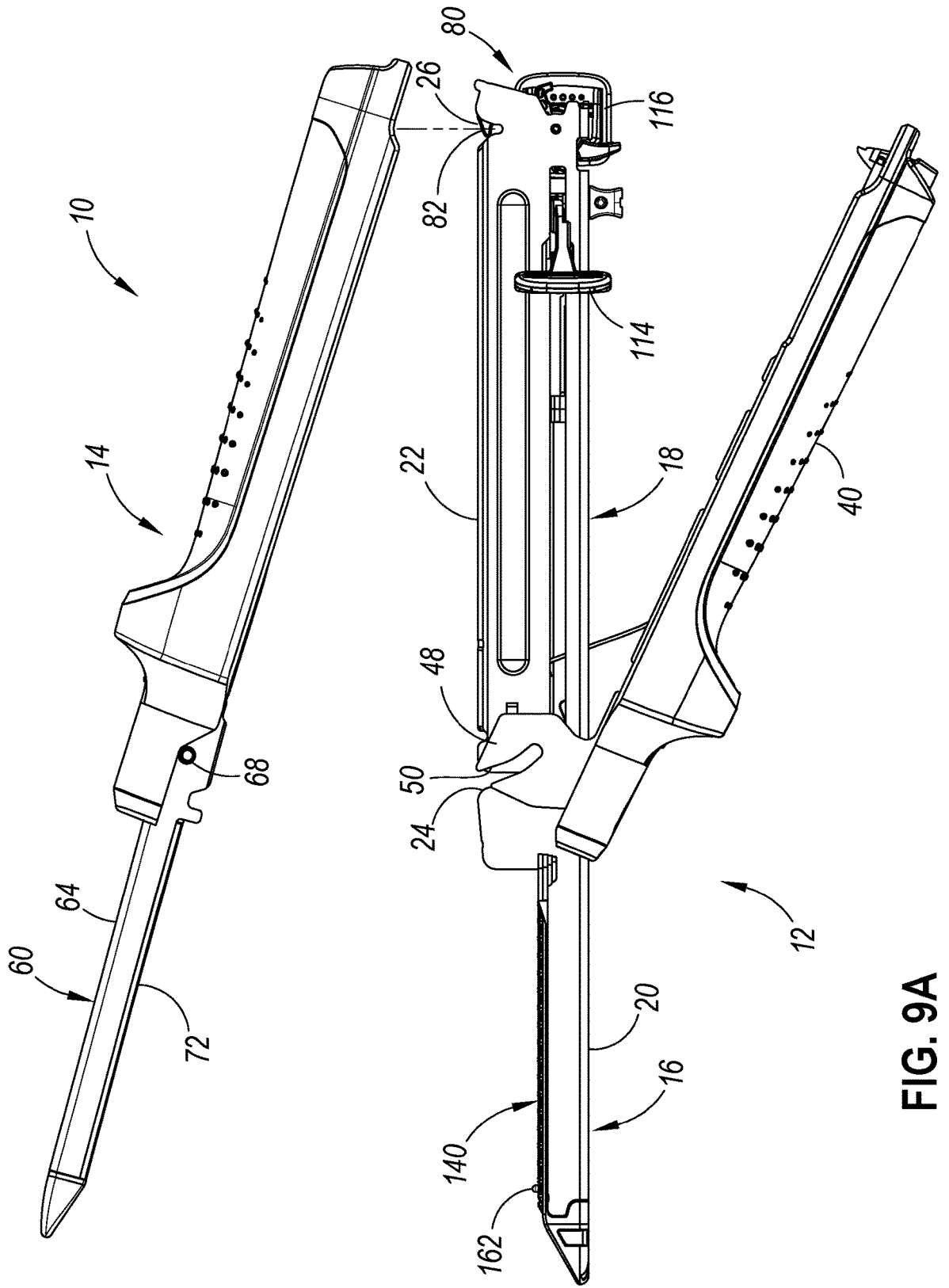
FIG. 9A depicts a side elevational view of the linear surgical stapler of FIG. 1, showing the stapler halves separated from one another with the clamp lever in the open position.
Figure 9B:
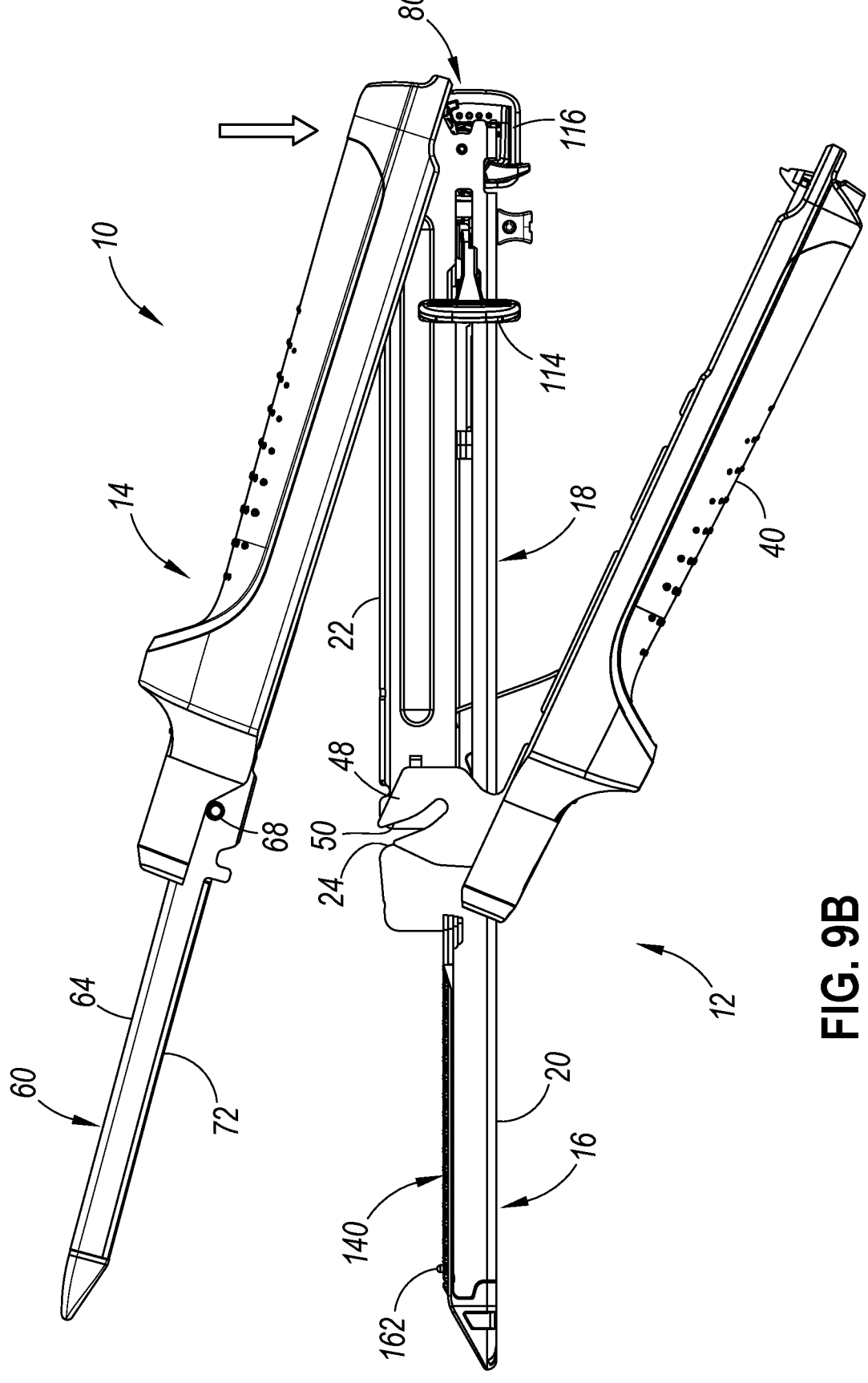
FIG. 9B depicts a side elevational view of the linear surgical stapler of FIG. 1, showing proximal ends of the stapler halves coupled together while the clamp lever is in the open position to provide the stapler in a "hang-open" state.
Figure 9C:
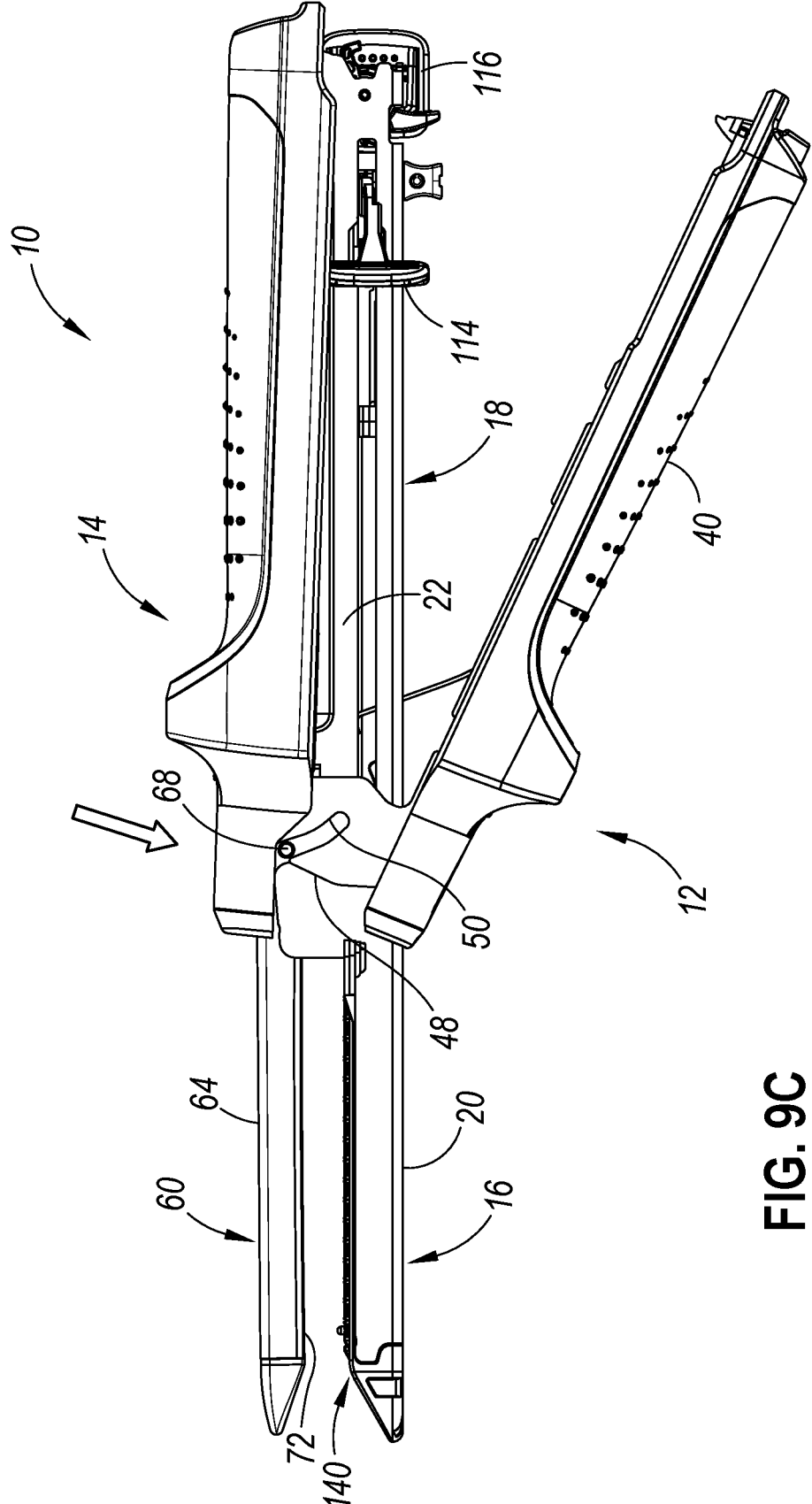
FIG. 9C depicts a side elevational view of the linear surgical stapler of FIG. 1, showing distal portions of the stapler halves having been approximated so that a distal pin of the anvil half is received by clamp lever jaws of the cartridge half.
Figure 9D:
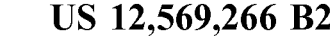
FIG. 9D depicts a side elevational view of the linear surgical stapler of FIG. 1, showing closure of the clamp lever to fully clamp the stapler halves together.

Clamp lever (40) is operable to pivot relative to cartridge channel (16) between an open position in which proximal end (46) of lever arm (44) is spaced from cartridge channel frame portion (18) as shown in FIGS. 9A-9C described below, and a closed position in which proximal end (46) confronts cartridge channel frame portion (18) as shown in FIG. 9D described below. Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 9C-9D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein.

Anvil half (14) of linear surgical stapler (10) includes a second elongate body and/or member in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
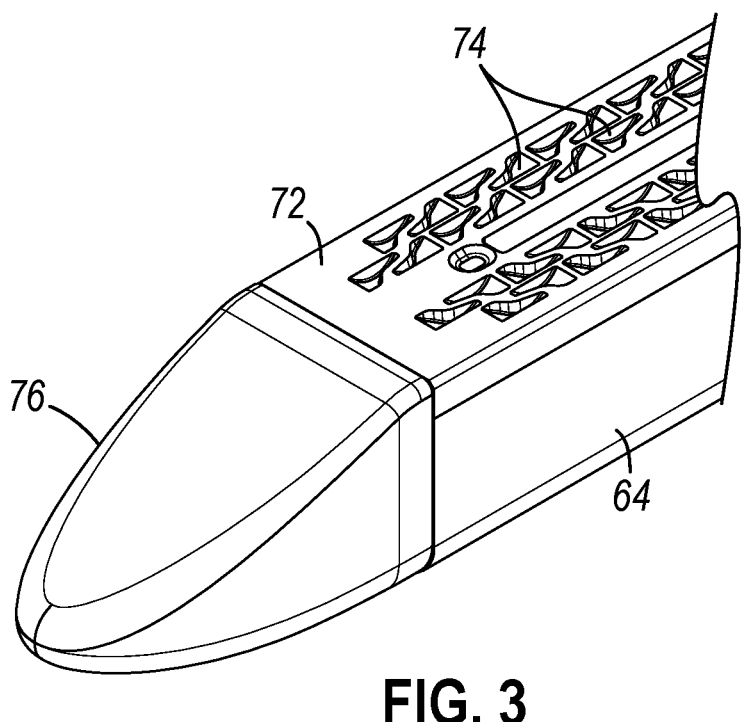
FIG. 3 depicts a perspective view of a distal end portion of the anvil half of the linear surgical stapler of FIG. 1.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, issued as U.S. Pat. No. 12,016,555 on Jun. 25, 2024, the disclosure of which is incorporated by reference herein. Anvil channel (60), anvil plate (72), and staple forming pockets (74) may be formed in one or more of the manners disclosed in U.S.

Pat. Nos. 11,229,433; 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022, issued as U.S. Pat. No. 12,016,555 on Jun. 25, 2024, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal frame portion (18) of cartridge channel (16) at a location distal to lower release button (92), and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
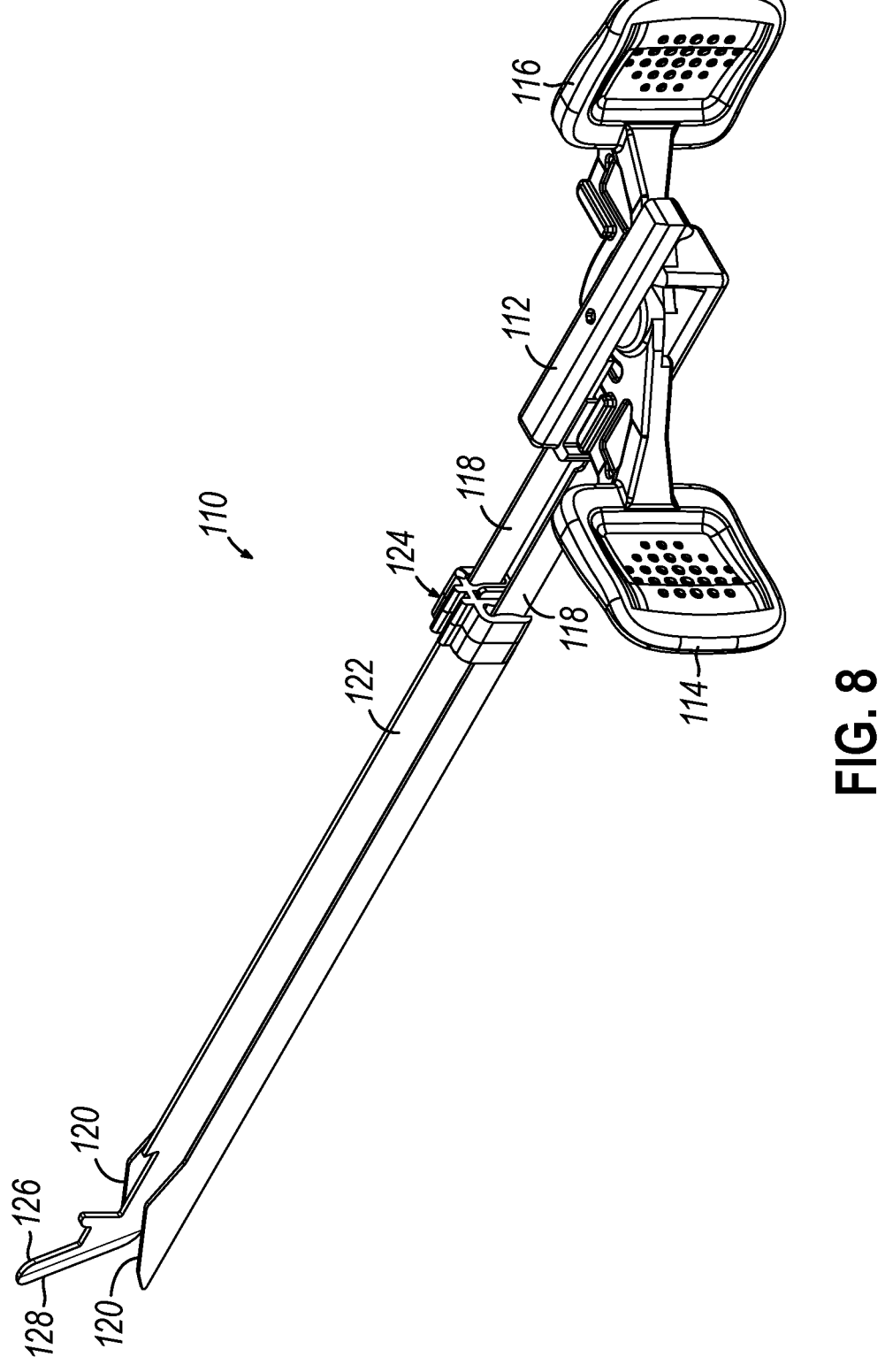
FIG. 8 depicts a perspective view of the firing assembly of FIG. 5.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (not shown) housed within staple cartridge (140) and actuate staple drivers (not shown) upwardly to thereby drive (or "fire") staples from cartridge (140) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Use of Linear Surgical Stapler

Figure 5:
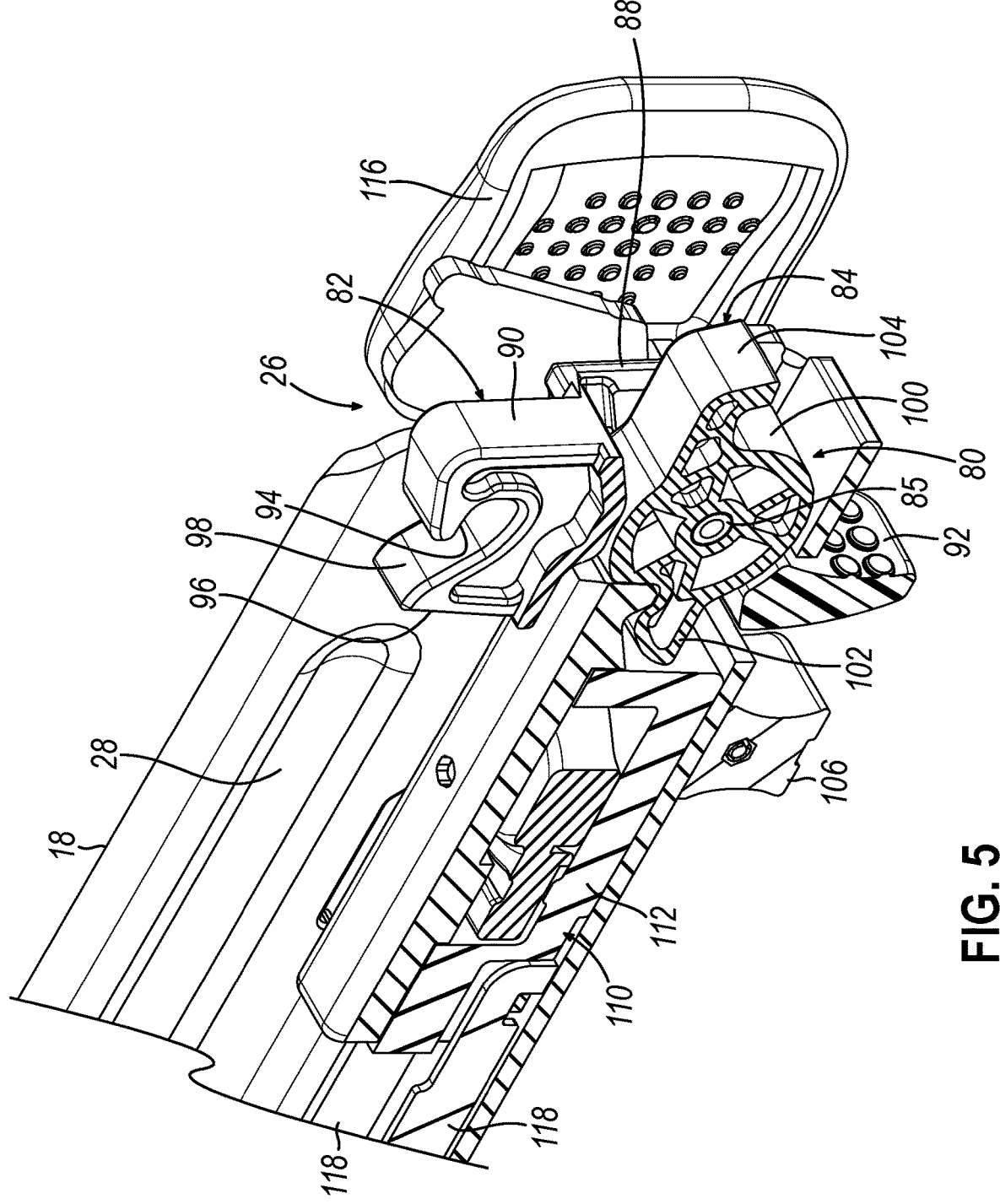
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.
Figure 6:
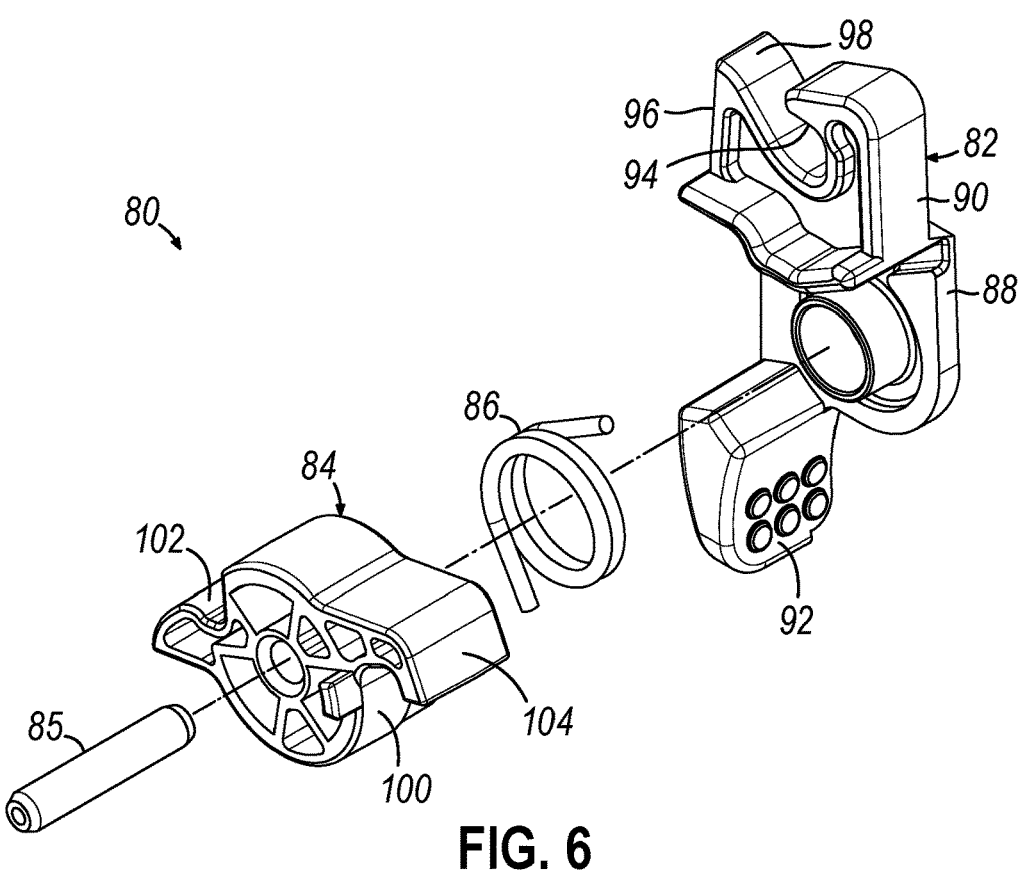
FIG. 6 depicts an exploded perspective view of the retaining assembly of FIG. 5.
Figure 7:
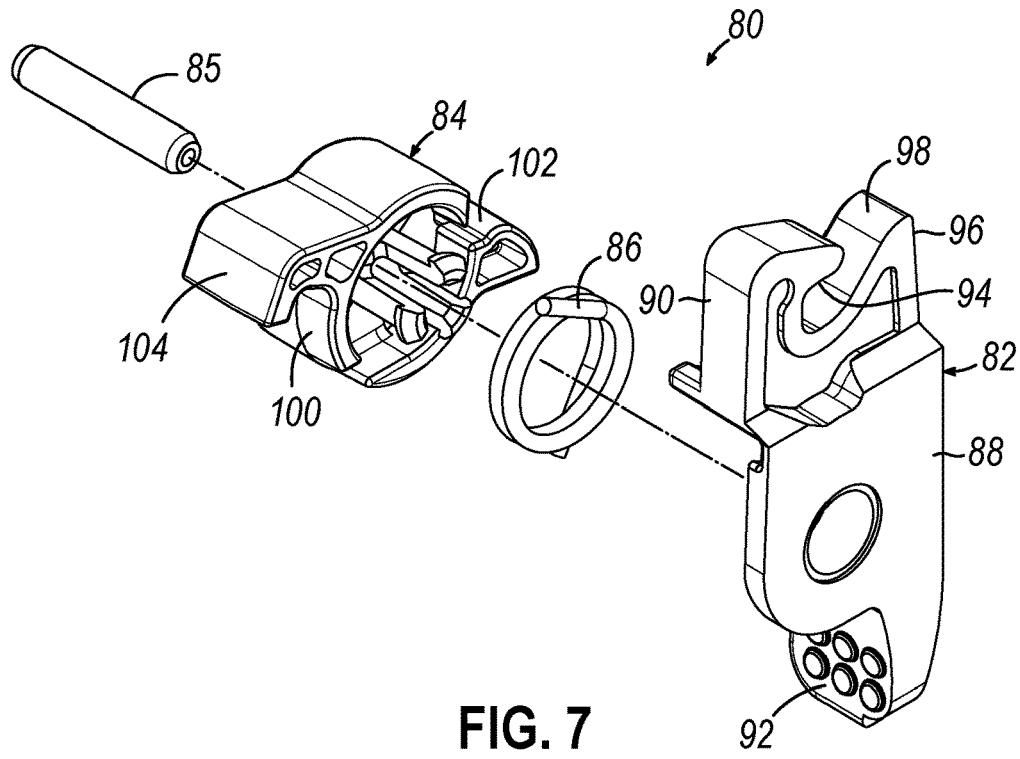
FIG. 7 depicts another exploded perspective view of the retaining assembly of FIG. 5.

FIGS. 9A-9E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with vertical slots (24) of cartridge channel side flanges (22). Additionally, firing assembly (110) is maintained in its proximal home position by detent member (84) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 9A-9B, the proximal ends of stapler halves (12, 14) are aligned with one another, and proximal anvil pin (70) is directed downwardly into proximal tapered notches (26) of cartridge channel (16) to engage latch finger (90) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 9B. With clamp lever (40) still in the open position as shown in FIG. 9B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

As shown in FIG. 9D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) and anvil plate (72). A slight transverse gap is defined between staple cartridge (140) and anvil plate (72) by a tissue gap post (162) of staple cartridge (140), thus accommodating the tissue therebetween with a predetermined degree of tissue compression. As shown in FIGS. 9A and 9B, tissue gap post (162) is disposed at a distal end of staple cartridge (140) and is configured to contact a distal end of anvil plate (72) when stapler (10) is in the fully clamped state shown in FIG. 19D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

Figure 9E:
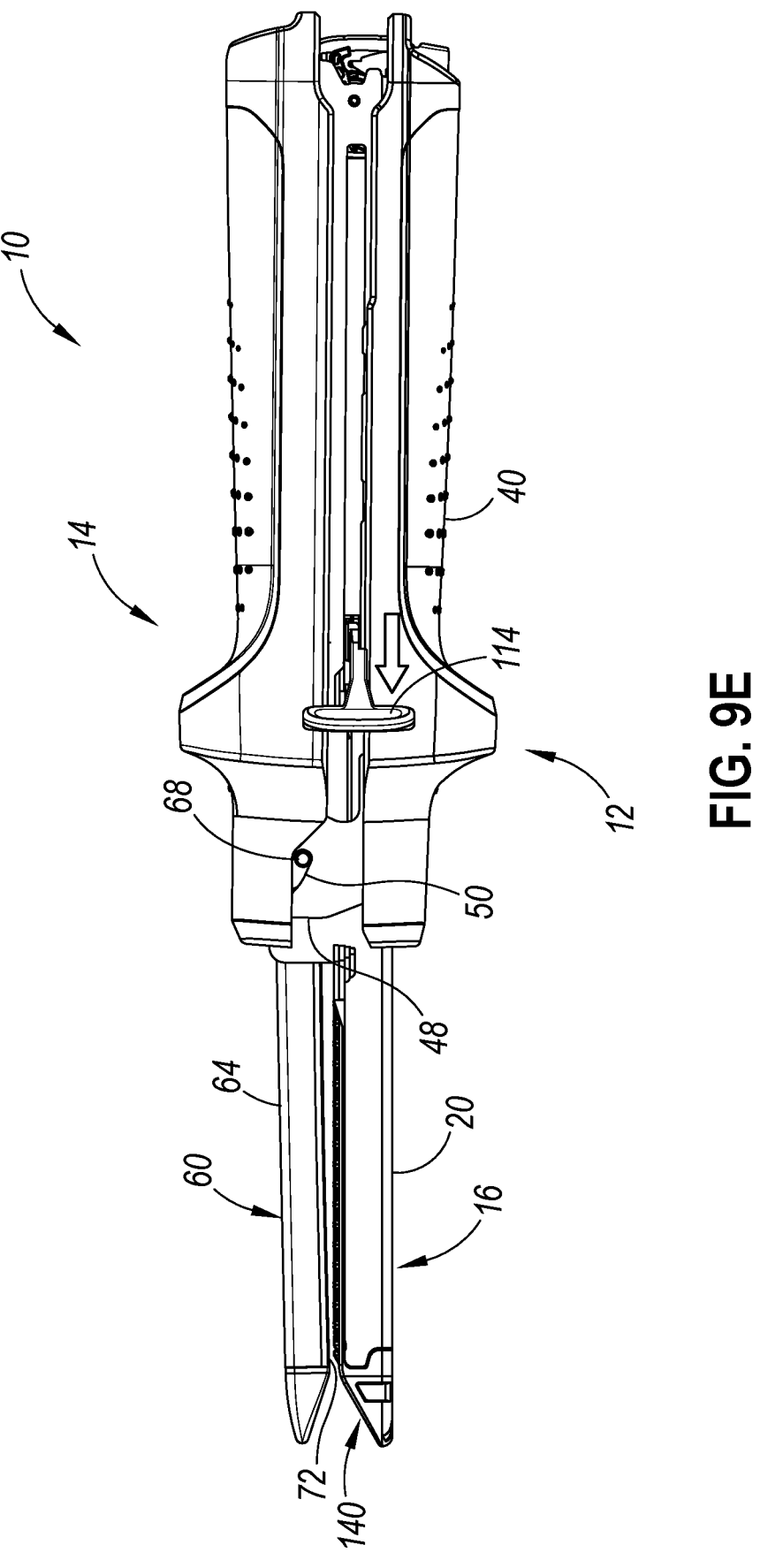
FIG. 9E depicts a side elevational view of the linear surgical stapler of FIG. 1, showing distal actuation of the firing assembly while the stapler halves are in the fully clamped state.

As shown in FIG. 9E, upon reaching the fully clamped state, stapler (10) may be fired by driving a deployed actuator (114, 116) of firing assembly (110) distally along proximal frame portion (18) of cartridge half (12). This action causes elongate beams (118, 122) of firing assembly (110) to translate distally through corresponding channels formed in staple cartridge (140) and thereby fire staples into the clamped tissue via cam ramps (120) and staple drivers (not shown), and simultaneously cut the clamped tissue with knife member (126). Following completion of the firing stroke, firing assembly (110) is returned to its proximal home position via the actuator (114, 116). Clamp lever latch member (54) may then be depressed to release the proximal end of clamp lever (40) from cartridge channel (16), thus permitting clamp lever (40) to be re-opened. Then, release button (92) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033, 266, incorporated by reference above.

C. Linear Surgical Stapler Having Anvil Strain Measuring Assembly

As mentioned above, anvil latch pin (68) of anvil half (14) is received within curved slots (50) of jaws (48) such that clamp lever (40) may pivot from the open position toward the closed position to thereby clamp anvil half (14) toward cartridge half (12) to thereby grasp and clamp tissue. Further, grasped tissue located between the stapling surfaces of staple cartridge (140) and anvil plate (72) may be severed and stapled.

Figure 10A:
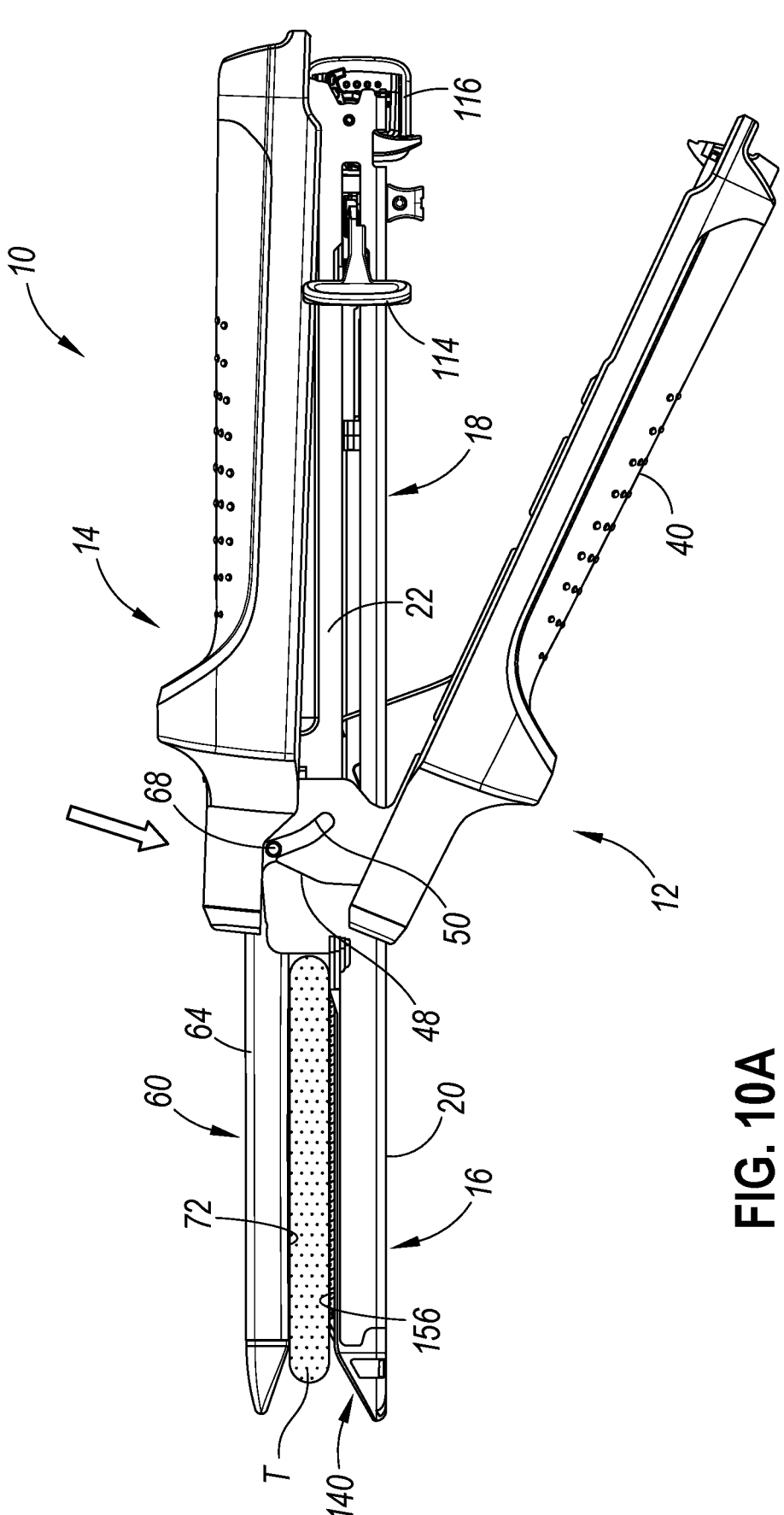
FIG. 10A depicts a side elevational view of the linear surgical stapler of FIG. 1, showing distal portions of the stapler halves having been approximated with tissue therebetween while the distal pin of FIG. 9C is initially received by clamp lever jaws of the cartridge half.
Figure 10B:
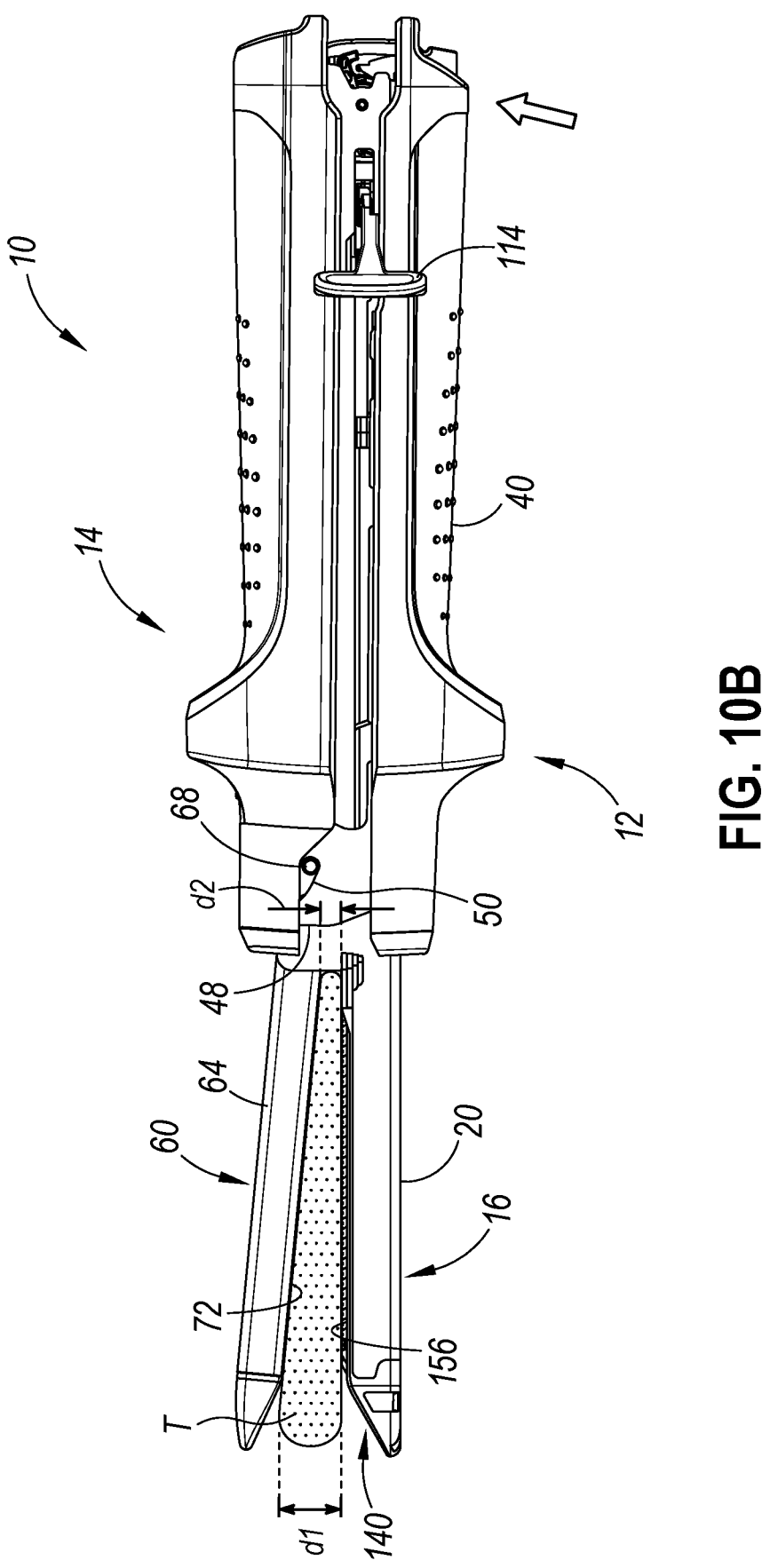
FIG. 10B depicts a side elevational view of the linear surgical stapler of FIG. 1, showing closure of the clamp lever to clamp the stapler halves together to grasp tissue therebetween.

In some instances, as shown between FIGS. 10A-10B, tissue grasped and clamped between staple cartridge (140) and anvil plate (72) may be too thick such that an undesirably large gap distance (d1) is defined between staple forming pockets (74) of anvil plate (72) and deck (156) of cartridge (140). Such a gap distance (d1) may also increase toward the distal end, as shown in FIG. 10B. If gap distance (d1) is too large, staples fired from staple cartridge toward anvil plate (72) may not suitably form, either creating malformed staples or "open" staples, either of which may fail to suitably engage staple forming pockets (74) of anvil plate (72). Further, in instances where grasped tissue is too thick, distal jaw portion (64) of elongated anvil channel (60) may become subject to large closure forces in order to clamp thicker tissue as compared to instances where an appropriate tissue thickness is clamped.

Figure 11A:
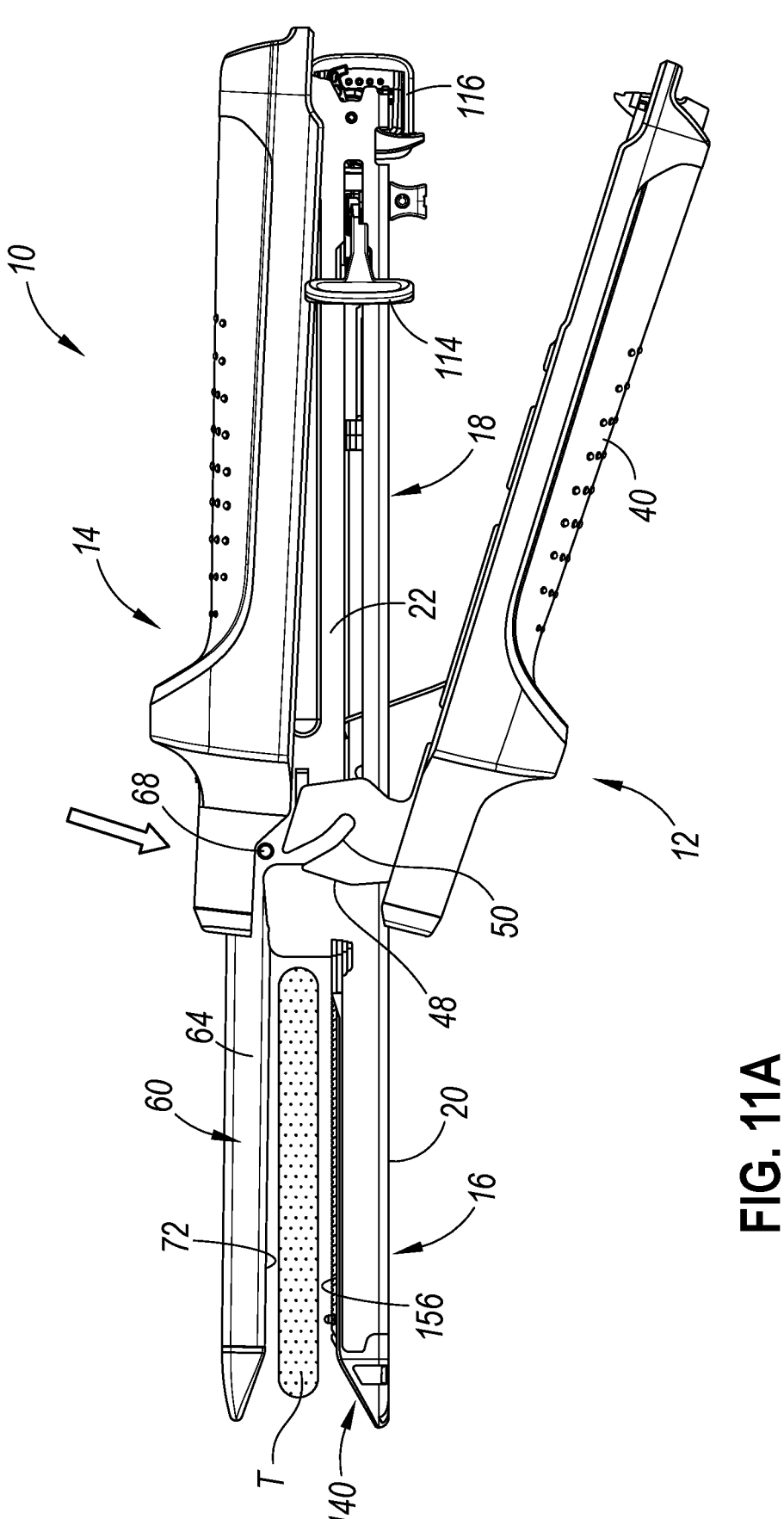
FIG. 11A depicts a side elevational view of the linear surgical stapler of FIG. 1, showing distal portions of the stapler halves having been approximated with tissue therebetween while the distal pin of FIG. 9C is misaligned with clamp lever jaws of the cartridge half.
Figure 11B:
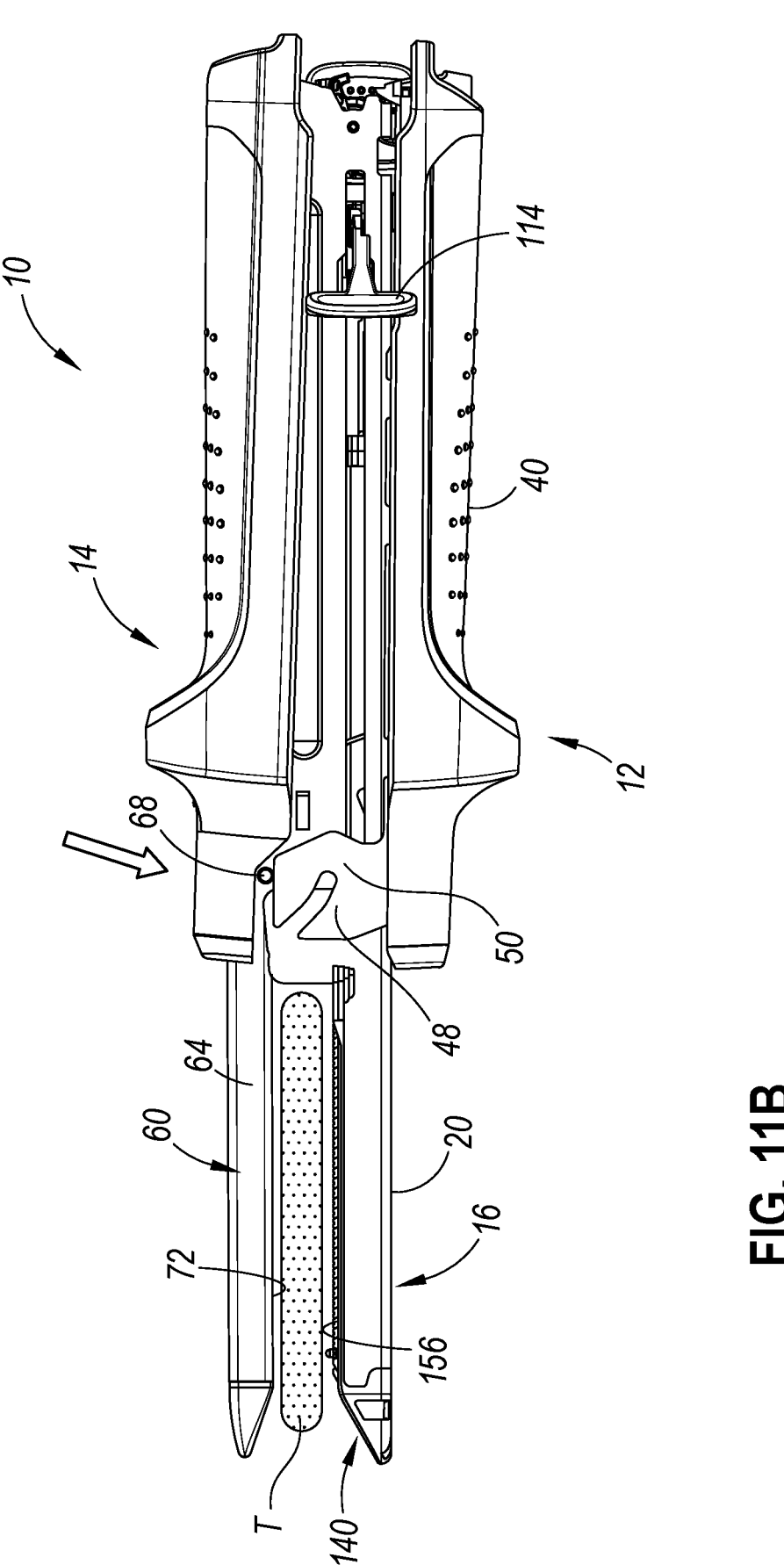
FIG. 11B depicts a side elevational view of the linear surgical stapler of FIG. 1, showing closure of the clamp lever while the distal pin of FIG. 9C is still misaligned with clamp lever jaws of the cartridge half.

As shown between FIGS. 11A-11B, in instances where clamp lever (40) is pivoted from the open position toward the closed position without anvil latch pin (68) received within curved slots (50) of jaws (48), tissue located between staple cartridge (140) and anvil plate (72) may never be properly clamped or grasped, leaving an undesirably large gap distance (d2). With an undesirably large gap distance (d2), staples fired from staple cartridge toward anvil plate (72) may not suitably form, for reasons similar to those described above. Further, in instances where anvil latch pin (68) is never received within curved slots (50) of jaws (48), distal jaw portion (64) of elongated channel (60) may experience little to no closure force, as clamp lever (40) is not suitably engaged with latch pin (68).

With clamp lever (40) providing the closure forces to clamp tissue via engagement with latch pin (68), closure forces are transferred to distal jaw portion (64) via latch pin (68). Therefore, portions of distal jaw portion (64) that are adjacent to latch pin (68) may incur larger values of strain deformation as compared to portions of distal jaw portion (64) further away from latch pin (68) during illustrative use in accordance with the teachings herein. The value of strain deformation of distal jaw portion (64) may be indicative of the closure forces acting on distal jaw portion (64) during illustrative use in accordance with the teachings herein. As mentioned above, if such closure forces are too high, this may be indicative of a too large a gap distance (d1) caused by too thick of tissue. As also mentioned above, if such closure forces are too low, this may also be indicative of too large a gap distance (d2) caused by anvil latch pin (68) never entering curved slots (50) of jaws (48). Therefore, it may be desirable to monitor the strain deformation of distal jaw (64), as such strain deformation may be indicative of a suitable or unsuitable gap distance, which may affect the staple formation quality of a fired staple.

Figure 12:
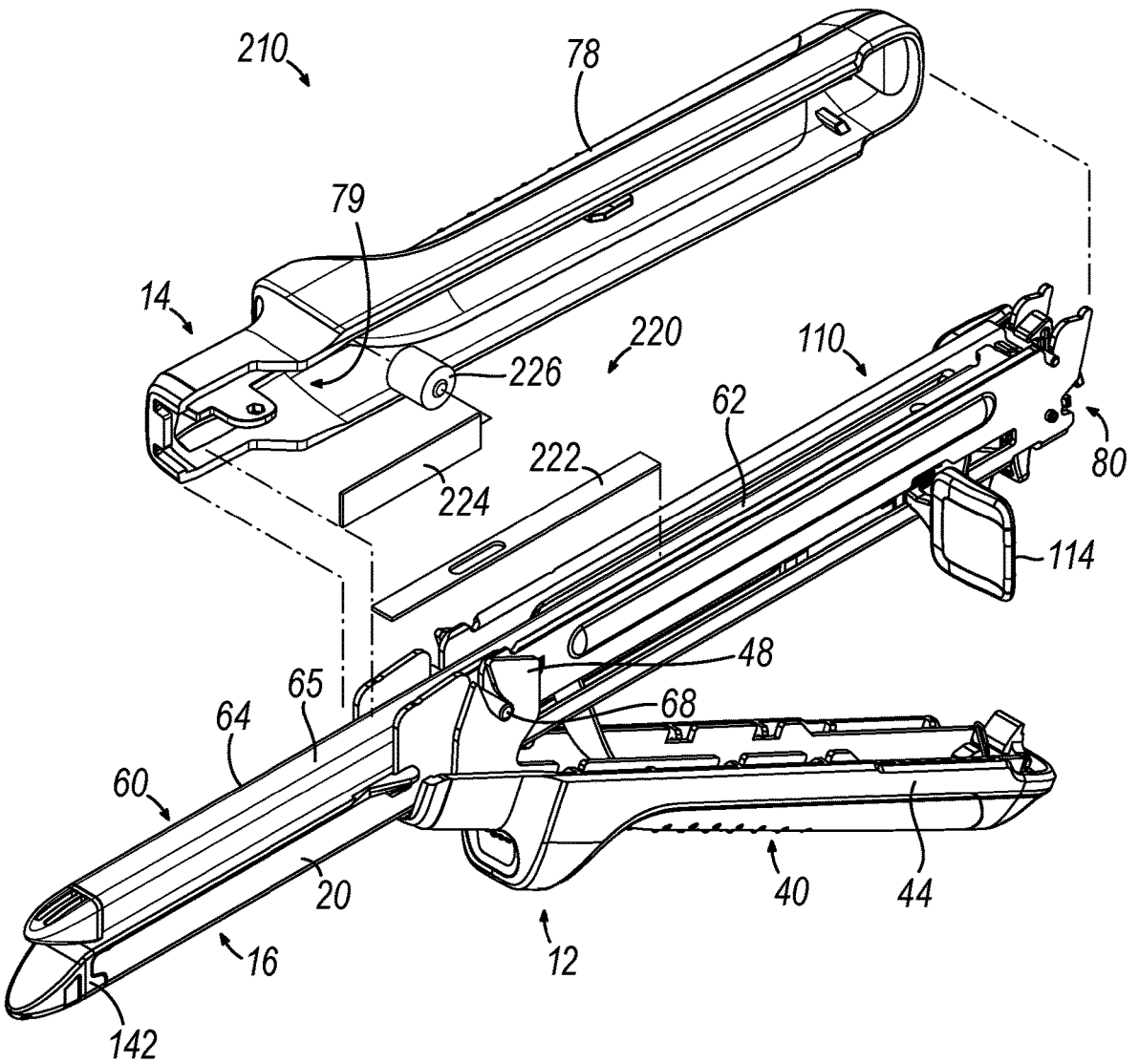
FIG. 12 depicts an exploded perspective view of an alternative linear surgical stapler having a cartridge half and an anvil half, with the anvil half having an anvil strain measuring assembly.

FIG. 12 shows an alternative illustrative linear surgical stapler (210) that is substantially similar to linear surgical stapler (10) described above, with differences elaborated below. Therefore, linear surgical stapler (210) includes cartridge half (12), anvil half (14), elongated cartridge channel (16), clamp lever (40), anvil channel (60), firing assembly (110), and replaceable staple cartridge (140). Additionally, linear surgical stapler (210) includes an anvil strain measuring assembly (220) housed within an interior cavity (79) defined by shroud (78) of anvil half (14). As will be described in greater detail below, anvil strain measuring assembly (220) is configured to measure the strain on a top surface (65) of elongate anvil channel (60) adjacent to anvil latch pin (68) during illustrative use of surgical stapler (210), compare the measured strain to one or more predetermined limit(s), and determine/communicate the risk of fired staples being malformed/open based on the comparison.

Figure 13:
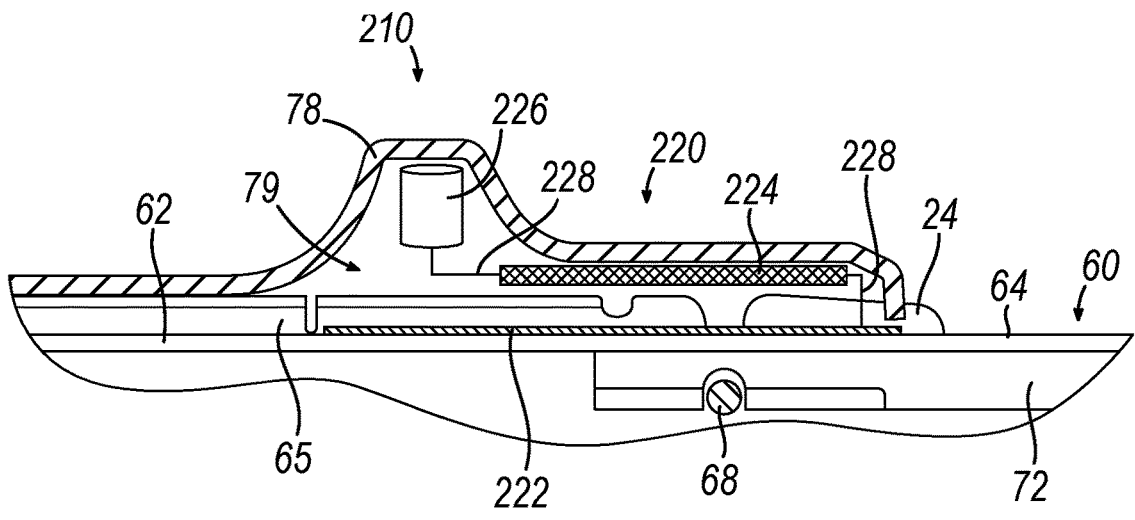
FIG. 13 depicts a cross-sectional view of a portion of the anvil half of FIG. 12.

Anvil strain measuring assembly (220) includes a strain gauge (222), a control assembly (224), and a power source, such as a battery (226). As best shown in FIG. 13, strain gauge (220) is in operative communication with control assembly (224) via electrical wiring (228). Similarly, control assembly (224) is in operative communication with battery (226) via electrical wiring (228). In the current example, battery (226) and control assembly (224) are suitably coupled to shroud (78) and are housed within interior cavity (79) defined by shroud (78). Battery (226) and control assembly (224) may be coupled to shroud (78) via any suitable means as would be apparent to one skilled in the art in view of the teaching herein. As will be described in greater detail below, strain gauge (222) is attached to top surface (65) of elongate anvil channel (60).

Battery (226) is configured to electrically power the necessary components of anvil strain measuring assembly (220). Battery (226) may include any suitable components as would be apparent to one skilled in the art in view of the teachings herein. In some instances, battery (226) may be connected to a switch (or other suitable mechanism) configured to selectively activate battery (226) such that a user may selectively activate anvil strain measuring assembly (220). Such a switch may be present on the outer surface of shroud (78) or any other suitable location. Therefore, a user may activate anvil strain measuring assembly (220) prior to illustrative use. Of course, battery (226) may be configured to activate anvil strain measuring assembly (220) in response to any other suitable activation method as would be apparent to one skilled in the art in view of the teachings herein.

Strain gauge (222) is suitably attached to a top surface (65) of elongate anvil channel (60). In particular, strain gauge (222) is located along a portion of top surface (65) that is adjacent to anvil latch pin (68). Strain gauge (222) is configured to measure the strain value at respective portions of anvil channel (60) in response to grasping and clamping tissue in accordance with the description herein. It should be understood that larger clamping forces required to suitably grasp tissue will result in larger measured strain measurement values; while smaller clamping forces required to suitably grasp tissue will result in smaller strain measurement values. Strain gauge (222) may include any suitable components and geometry as would be apparent to one skilled in the art in view of the teachings herein. Further, strain gauges (222) may be attached to top surface (65) of elongated anvil channel (60) using any suitable means as would be apparent to one skilled in the art in view of the teachings herein.

As mentioned above, deviations in strain of anvil channel (60) in response to grasping and clamping tissue may be the largest (i.e., more pronounced) at portions of anvil channel (60) adjacent to anvil latch pin (68) due to jaws (48) of clamp lever (40) applying the clamping force to anvil channel (60) via anvil latch pin (68). Therefore, strain gauge (222) being located at or around portions of elongated anvil channel (60) adjacent to anvil latching pin (68) may provide the benefit of measuring strain deviations associated with, or strongly indicative to, clamp lever (40) driving anvil channel (60) into a clamped configuration during illustrative use in accordance with the description herein.

As mentioned above, strain gauge (222) is in operative communication with control assembly (224) via electrical wiring (228). Strain gauge (222) is configured to communicate the strain signal indicative of the measured strain value to control unit (224). Control assembly (224) is configured to compare the measured strain value to one or more predetermined limits. Control assembly (224) may generate a communication signal in response to the comparison of the measured strain value to the one or more predetermined limits.

For example, a first predetermined limit may be indicative of clamp lever (40) applying the necessary clamping force to clamp tissue having a maximum acceptable tissue thickness associated with a generally acceptable maximum gap distance. If the measured strain value from strain gauge (222) is above the first predetermined limit, this may be indicative that the clamped tissue between deck (156) (see FIGS. 10A-11B) and anvil plate (72) is too thick and creates a gap distance greater than the generally acceptable maximum gap distance. In other words, if the measured stain value is above the first predetermined limit, this may be indicative that fired staples have an unacceptably high risk of being malformed or open.

Control assembly (224) includes suitable electrical components necessary to receive strain signals from strain gauge (222), compare the received strain signals to predetermined limit(s), and generate a communication signal in response to such a comparison. Control assembly (224) may include printed circuit board (PCB), suitable memory, and/or suitable processing means to function in accordance with the description herein.

Figure 14:
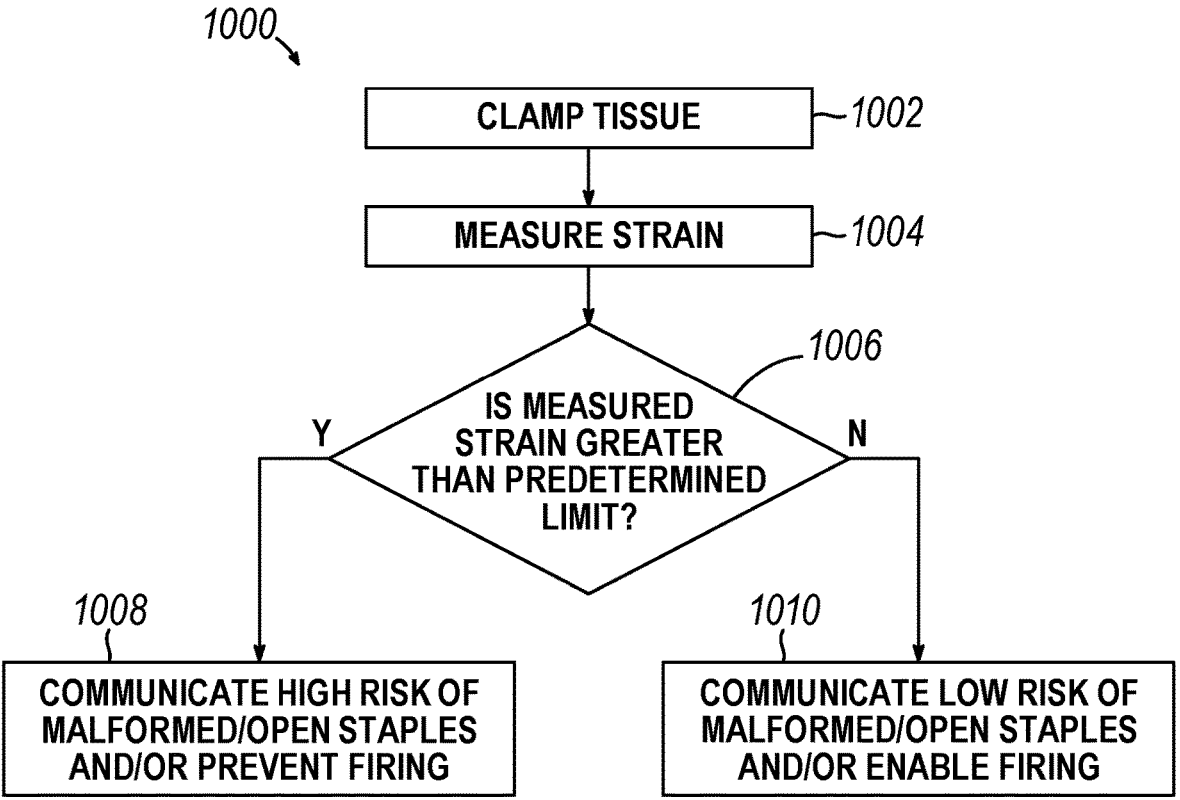
FIG. 14 depicts a flowchart of an illustrative method of use of a linear surgical stapler having an anvil strain measuring assembly.

FIG. 14 shows an illustrative method (1000) of using linear surgical stapler (210). First, a user may clamp tissue (1002) between deck (156) (see FIGS. 10A-11B) of staple cartridge (140) and anvil plate (72) of elongate anvil channel (60) by utilizing clamp lever (40) in accordance with the teachings herein. In such an instances, anvil latching pin (68) is driven into the clamped configuration via suitable engagement with curved slot (50) defined by opposed jaws (48) of clamp lever (40). As mentioned above, generally, thicker clamped tissue results in both larger clamping forces (and resulting larger strains on anvil channel (60)) and larger gap distances (d1, d2) between anvil plate (72) and deck (156) (see FIGS. 10A-11B).

While tissue is suitably clamped, strain gauge (222) of anvil strain measuring assembly (220) measures (1004) the resulting strain on portions of top surface (65) adjacent to anvil latching pin (68). A signal indicative of the measured strain on top surface (65) of anvil channel (60) is communicated to control assembly (224), which then compares (1006) the measured strain from strain gauge (222) to a predetermined limit stored on control assembly (224). In the current illustrative method, control assembly (224) asks if the measured strain is greater than the predetermined limit. Such a predetermined limit may be associated with a maximum acceptable gap distance between deck (156) (see FIGS. 10A-11B) and anvil plate (72).

If the measured strain is greater than the predetermined limit, control assembly (224) then communicates (1008) the high risk of malformed and/or open staples if device is fired. Additionally and/or alternatively, control assembly (224) may prevent firing in accordance with the teachings herein. If the measured strain is smaller than the predetermined limit, control assembly (224) then communicates (1010) the low risk of malformed and/or open staples if device is fired. Additionally and/or alternatively, control assembly (224) may allow firing in accordance with the teachings herein. Any suitable means of communicating such results may be used as would be apparent to one skilled in the art in view of the teachings herein.

Figure 15:
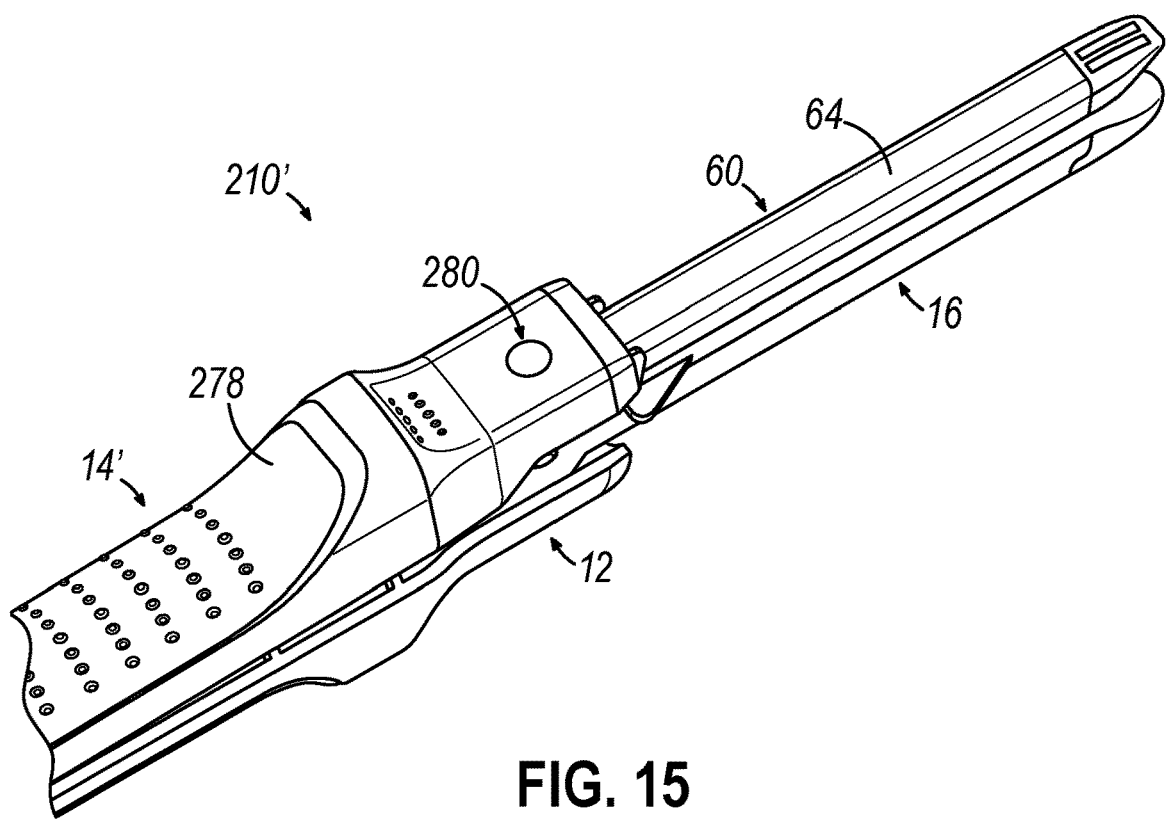
FIG. 15 depicts a perspective view of an alternative linear surgical stapler having a clamp quality indicator indicating distal portions of the stapler halves are properly grasping tissue such that the risk of malformed or open staples is low.
Figure 16:
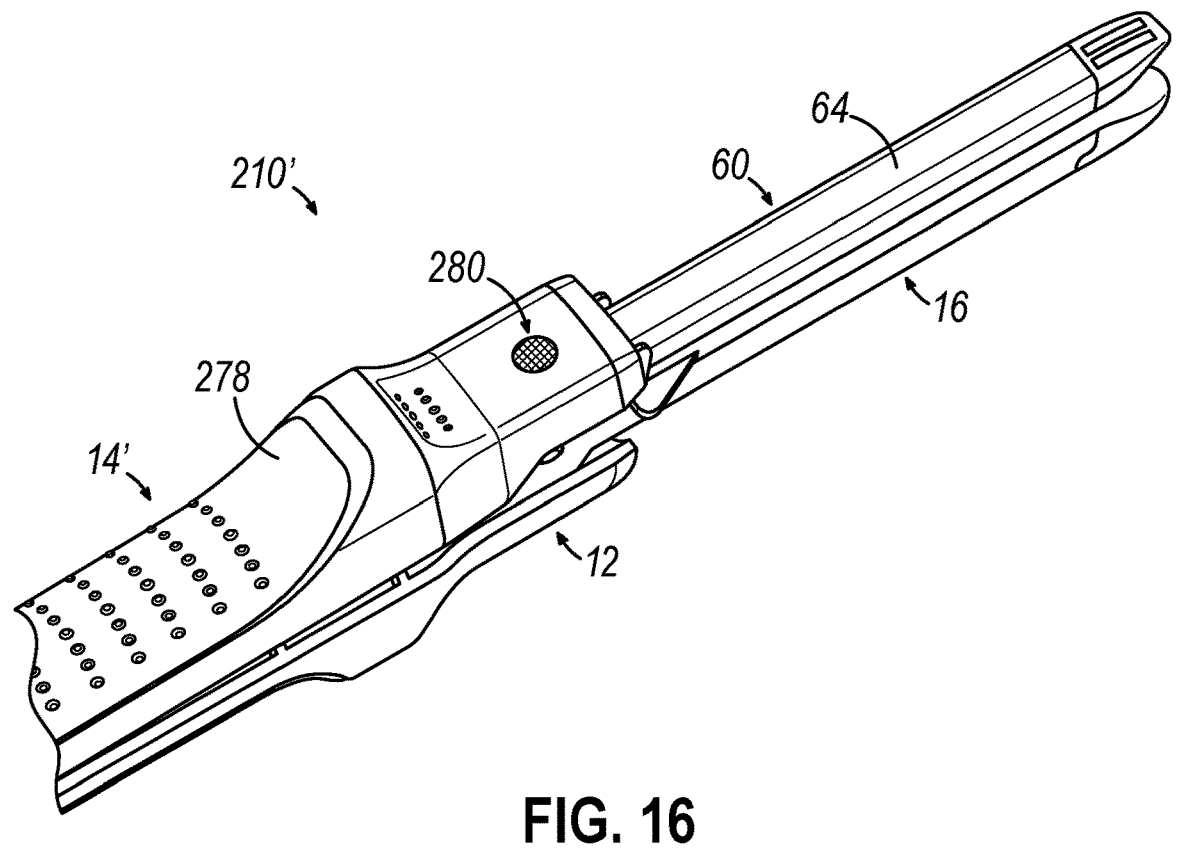
FIG. 16 depicts a perspective view of the linear surgical stapler of FIG. 15, where the clamp quality indicator of FIG. 15 indicates distal portions of the stapler halves are improperly grasping tissue such that the risk of malformed or open staples is high.

FIGS. 15-16 show an illustrative linear surgical stapler (210') that is substantially similar to linear surgical stapler (210) described above, except that anvil half (14') includes an alternative shroud (278). Shroud (278) is substantially similar to shroud (78) described above, with differences elaborated herein. Therefore, it should be understood that shroud (278) houses anvil strain measuring assembly (220). Additionally shroud (278) includes a visual clamp quality indicator (280) which is in communication with control assembly (224) via electrical wiring (228). Visual clamp quality indicator (280) may also be in suitable communication with battery (226) such that battery (226) may electrically power visual clamp quality indicator (280).

As best seen between FIGS. 15-16, visual clamp quality indicator (280) may illuminate a first color in order to communicate the measured strain is within an acceptable range (e.g., below the predetermined limit), thereby indicating an acceptable gap distance; while visual clamp quality indicator (280) may illuminate a second color in order to communicate the measured strain is out of the acceptable range (e.g., above the predetermined limit). Therefore, during illustrative use, an operator may look at visual clamp quality indicator (280) after clamping tissue, yet prior to firing staples and/or severing tissue, in order to visually confirm tissue is suitably clamped in accordance with the description herein.

While in the current example, visual clamp quality indictor (280) illuminates two different colors in order to communicate whether or not an acceptable gap distance between anvil plate (72) and staple deck (156) is present, any other suitable means may be utilized as would be apparent to one skilled in the art in view of the teaching herein. For example, visual indictor (280) may flash when the measured strain is out of an acceptable range during illustrative use, and illuminate continuously when the measure strain is within the acceptable range during illustrative use. In some instances, visual indicator (280) may not provide visual confirmation, but instead may provide other suitable forms of feedback, such as audible and/or tactile feedback.

Figure 17:
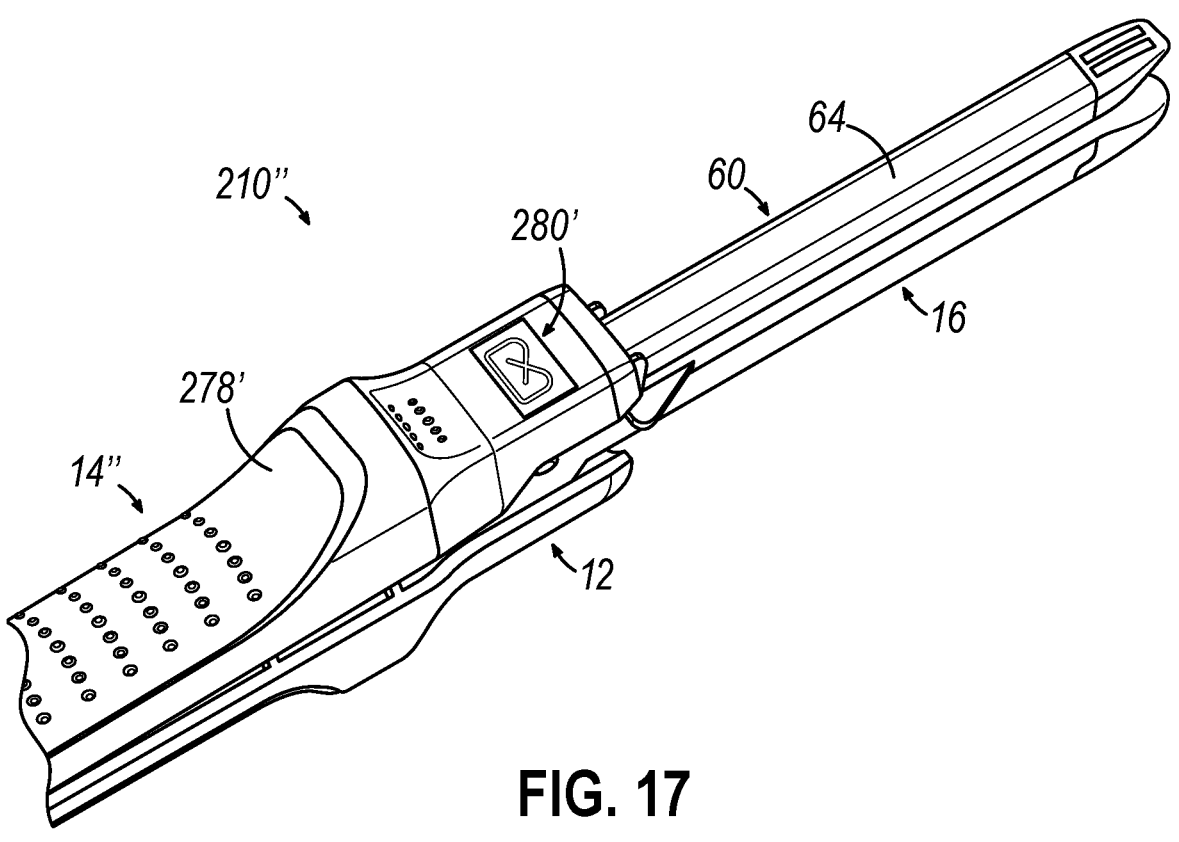
FIG. 17 depicts a perspective view of an alternative linear surgical stapler having a clamp quality indicator indicating distal portions of the stapler halves are properly grasping tissue such that the risk of malformed or open staples is low.
Figure 18:
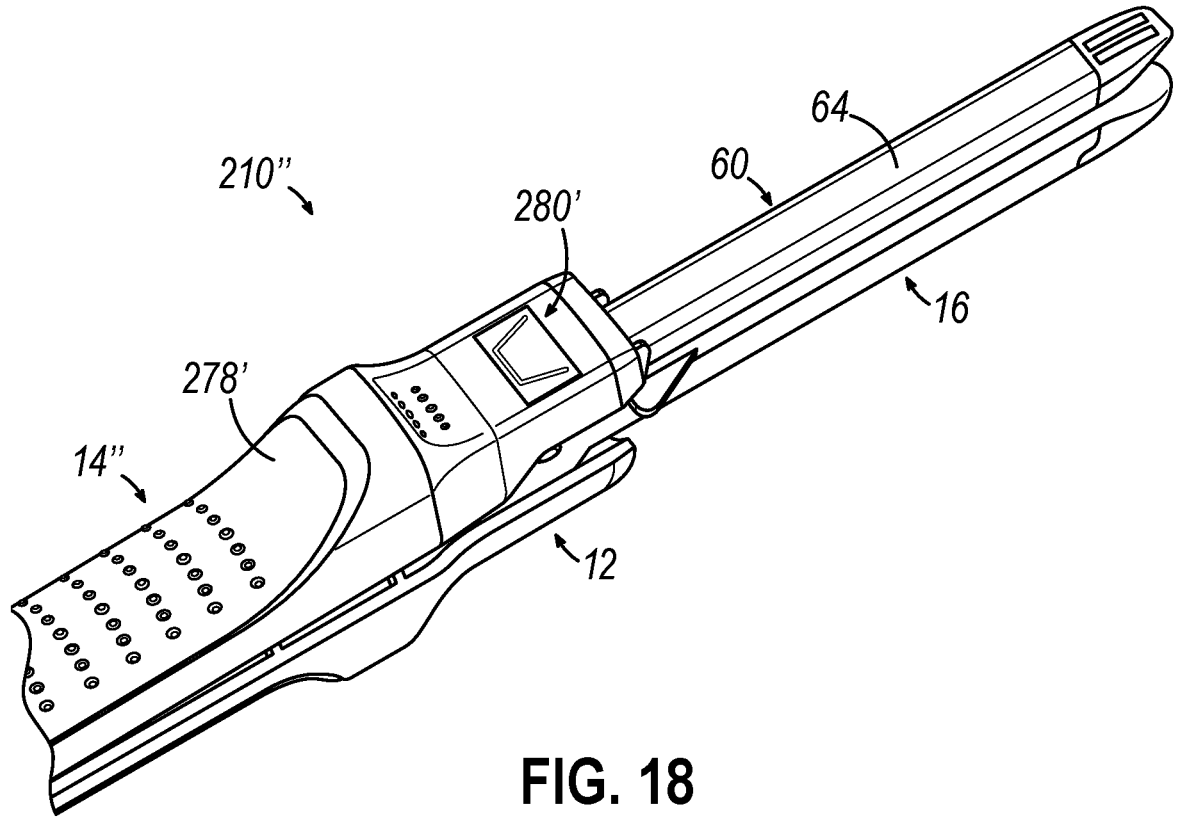
FIG. 18 depicts a perspective view of the linear surgical stapler of FIG. 17, where the clamp quality indicator of FIG. 17 indicates distal portions of the stapler halves are improperly grasping tissue such that the risk of malformed or open staples is high.

FIGS. 17-18 show an illustrative linear surgical stapler (210'') that is substantially similar to linear surgical stapler (210, 210') described above, except that anvil half (14'') includes an alternative shroud (278'). Shroud (278') is substantially similar to shroud (78, 278) described above, with differences elaborated herein. Therefore, it should be understood that shroud (278') houses anvil strain measuring assembly (220). Additionally shroud (278') includes a visual clamp quality indicator (280') which is in communication with control assembly (224) via electrical wiring (228). Visual clamp quality indicator (280') is also be in suitable communication with battery (226) such that battery (226) may electrically power visual clamp quality indicator (280').

As best seen between FIGS. 17-18, visual clamp quality indicator (280') displays a properly formed "B" staple in order to communicate the measured strain is within an acceptable range (e.g., below the predetermined limit), thereby indicating an acceptable gap distance; while visual clamp quality indicator (280') displays an open staple in order to communicate the measured strain is out of the acceptable range (e.g., above the predetermined limit). Therefore, during illustrative use, an operator may look at visual clamp quality indicator (280') after clamping tissue, yet prior to firing staples and/or severing tissue, in order to visually confirm tissue is suitably clamped in accordance with the description herein.

FIGS. 19-20 show an illustrative linear surgical stapler (210''') that is substantially similar to linear surgical stapler (210, 210', 210'') described above, except that anvil half (14''') includes an alternative shroud (278''). Shroud (278'') is substantially similar to shroud (78, 278, 278') described above, with differences elaborated herein. Therefore, it should be understood that shroud (278'') houses anvil strain measuring assembly (220). Additionally shroud (278'') includes a visual clamp quality indicator (280'') which is in communication with control assembly (224) via electrical wiring (228). Visual clamp quality indicator (280'') is also be in suitable communication with battery (226) such that battery (226) may electrically power visual clamp quality indicator (280'').

As best seen between FIGS. 19-20, visual clamp quality indicator (280'') displays an estimated percentage for the chance/odds properly formed staples may be formed based at least in part on the measured strain (e.g., within an acceptable range associated with a 99% success rate, at a measured strain value associated with a 40% success rate, etc.). Therefore, during illustrative use, an operator may look at visual clamp quality indicator (280'') after clamping tissue, yet prior to firing staples and/or severing tissue, in order to visually confirm tissue is suitably clamped in accordance with the description herein.

As mentioned above, in some instances, clamp lever (40) is pivoted from the open position toward the closed position without anvil latch pin (68) received within curved slots (50) of jaws (48). With anvil latch pin (68) disengaged from clamp lever (40) (e.g., clamp lever (40) imparts to clamping force onto anvil channel (60)), the measured strain on top surface (65) for anvil channel (60) may be substantially zero (providing for noise measurements from strain gauge (222) and/or negligible strain generated from a user manually closing halves (12, 14) together, etc.). In such instances, tissue located between staple cartridge (140) and anvil plate (72) may never be properly clamped or grasped, leaving an undesirably large gap distance (d2).

FIG. 21 shows an illustrative method (1100) of using linear surgical stapler (210, 210', 210'', 210''') where anvil strain measuring assembly (220) accounts for the possibility that anvil latch pin (68) is not suitable received within curved slots (50) of jaws (48). First, a user may clamp tissue (1102) between deck (156) (see FIGS. 10A-11B) of staple cartridge (140) and anvil plate (72) of elongate anvil channel (60). Next, anvil strain measuring assembly (220) measures strain (1104) on top surface (65) of anvil channel (60) in accordance with the description herein. A signal indicative of the measured strain on top surface (65) of anvil channel (60) is communicated to control assembly (224), which then compares (1106) the measured strain from strain gauge (222) to a predetermined limit stored on control assembly (224).

If the measured strain is greater than the predetermined limit, this may be indicative that tissue grasped is too thick, thereby leaving an undesirably large gap distance (similar to gap distance (d1) shown in FIG. 10B). Therefore, if the measured strain is greater than the predetermined limit, control assembly (224) communicates (1108) the high risk of malformed and/or open staples if device is fired. Additionally, and/or alternatively, control assembly (224) may prevent firing in accordance with the teachings herein.

If the measured strain is smaller than the predetermined limit, control assembly (224) then compares (1110) the measured strain from strain gauge (222) to see if the measured strain is substantially zero. If the measured strain is substantially zero, this may be indicative that anvil latching pin (68) is not suitably housed within curved slots (50) of jaws (48), thereby leaving an undesirably large gap distance (similar to gap distance (d2) shown in FIG. 11B). Therefore, if the measured strain is substantially zero, control assembly (224) communicates (1010) the high risk of malformed and/or open staples if device is fired. As shown in FIG. 22, in instances where visual clamp quality indicator (280'') is used, indicator (280'') may show there is a 0% chance (or a negligible chance) of successful staple formation when the measured strain is substantially zero. Additionally and/or alternatively, control assembly (224) may prevent firing in accordance with the teachings herein.

If the measured strain is not greater than the predetermined limit, and is not substantially zero, then control assembly (224) determines that the measured strain is below the predetermined limit and above substantially zero, thereby determining that the measured strain is within an acceptable range (1114). In such instances, control assembly (224) communicates (1116) the low risk of malformed and/or open staples if device is fired. Additionally, and/or alternatively, control assembly (224) may allow firing in accordance with the teachings herein. Any suitable means of communicating such results may be used as would be apparent to one skilled in the art in view of the teachings herein.

Due to tolerance stacks in the manufacturing process of linear surgical stapler (10, 210, 210', 210'', 210'''), the strain imparted on a first linear surgical stapler (10, 210, 210', 210'', 210''') associated with a suitable gap distance may be different from the strain imparted on a second linear surgical stapler (10, 210, 210', 210'', 210''') associated with the same suitable gap distance. Therefore, it may be desirable to customize the predetermined limit(s) used by anvil strain measuring assembly (220) described above, for a specific linear surgical stapler (10, 210, 210', 210'', 210''').

FIG. 23 shows an illustrative method (1200) of determining the predetermined limit used by anvil strain measuring assembly (220). First, during the manufacturing process, an assembled linear surgical stapler (10, 210, 210', 210'', 210''') may be clamped on a load cell in order to measure the clamping forces between anvil plate (72) and staple deck (156) to ensure such clamping forces are within an acceptable range. Additionally, while linear surgical stapler (10, 210, 210', 210", 210''') is clamped onto the load cell, the anvil strain measured by strain gauge (222) may also be measured (1204). It should be understood that any suitable components may be used to acquire the strain gauge (222) measurement as would be apparent to one skilled in the art in view of the teachings herein. Next, with the measured (1204) anvil strain acquired during illustrative clamping of stapler (10, 210, 210', 210", 210''') on load cell ensuring acceptable clamping force, the measured (1204) anvil strain may be utilized to generate (1206) a uniquely characterized device parameter (e.g., the predetermined limit used by anvil strain measuring assembly (220) in accordance with the teachings herein). Next, the uniquely characterized device parameter may be stored on and/or written (1208) to the control assembly (224) of anvil strain measuring assembly (220) for illustrative use.

As mentioned above, in some instances, control assembly (224) may prevent firing of stapler (10, 210, 210', 210", 210''') in instances where anvil strain measuring assembly (220) determines the measured anvil strain is outside an acceptable anvil strain range associated with suitable staple formation. FIGS. 24A-24B show an illustrative linear surgical stapler (310) configured to lockout firing of staples until a measured anvil strain is within an acceptable range associated with suitable staple formation.

Stapler (310) is substantially similar to stapler (10, 210, 210', 210", 210''') described above, with differences elaborated herein. Stapler (310) includes an anvil strain measuring assembly (320) that is substantially similar to anvil strain measuring assembly (220) described above, with differences elaborated herein. Anvil strain measuring assembly (320) includes a strain gauge (322), a control assembly (324), a battery (326), and electrical wiring (328); which are substantially similar to strain gauge (222), control assembly (224), battery (226), and electrical wiring (228) described above. Additionally, anvil strain measuring assembly (320) includes a solenoid lockout (330) in communication with control assembly (324) via electrical wiring (328).

Solenoid lockout (330) is configured to actuate between a locked (see FIG. 24A) and unlocked configuration (see FIG. 24B). In the locked configuration, solenoid lockout (330) is configured to selectively prevent distal actuation of distal cutting edge (126). In the unlocked configuration, solenoid lockout (330) is configured to allow distal actuation of distal cutting edge (126). Solenoid lockout (330) is biased toward the locked configuration.

As mentioned above, solenoid lockout (330) is in communication with control assembly (324). Battery (326) is configured to power solenoid lockout (330). When control assembly (324) receives a measured strain from strain gauge (322) within the predetermined range associated with suitable staple formation, control assembly (324) instructed solenoid lockout (330) to actuate from the locked continuation to the unlocked configuration, thereby enabling distal actuation of distal cutting edge (126) and firing assembly (110). Therefore, solenoid lockout (330) inhibits firing of firing assembly (110) unless the measured strain from strain gauge (322) is within an acceptable range associated with suitable staple formation.

It should be understood that while anvil strain measuring assemblies (220, 320) are used in the context of linear surgical staplers (10, 210, 210', 210", 210''', 310), anvil strain measuring assembly (220, 320) may be readily incorporated into any other suitable surgical staples. FIGS. 25-26 show an anvil strain measuring assembly (402) associated with an anvil (410) of a laparoscopic surgical stapler (400) having anvil (410) and a staple cartridge jaw (450) forming an end effector attached to the distal end of a shaft assembly (420) dimensioned to be laparoscopically inserted into a patient.

Anvil (410) defines long channel (414) located on a lateral side of anvil (410) housing an array of strain sensors (404) connected to each other via electrical wire (406) that extends proximally from anvil (410) and shaft assembly (420) into a control unit (408) (such as a surgeon's console or electrical control unit housed within an optional handle portion of the laparoscopic instrument or external from instrument). As anvil surface (412) of anvil (410) grasping tissue (T) with staple cartridge jaw (450), stain sensors (404) measure the strain within anvil (410) and communicate that strain to control unit (408) via wires (406). Control unit (408) may use the measured stain in similar fashion as control assembly (224, 324) described above, thereby enabling control unit (408) to predict if a suitable gap distance is present between anvil surface (412) and staple cartridge jaw (450) when tissue is suitably clamped. Control unit (408) may notify a user and or prevent firing of end effector in similar fashion as control assembly (224, 324) described above.

II. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a first elongate member having a distal portion configured to present a first stapling surface; (b) a second elongate member having a distal portion configured to present a second stapling surface, wherein the first and second elongate members are configured to releasably couple together to enable the first and second stapling surfaces to cooperate to clamp and staple tissue with a plurality of staples; (c) a clamp member, wherein the clamp member is movable relative to the first and second elongate members from a first position to a second position to approximate the first and second stapling surfaces for clamping tissue; (d) a latch member configured to transition from an unlatched state to a latched state to releasably retain the clamp member in the second position; (e) a firing assembly, wherein the firing assembly is actuatable from a home position to fire the staples into the clamped tissue; and (f) a strain measuring assembly associated with the first elongated member, wherein the strain measuring assembly is configured to: (i) measure a strain value on the first elongate member, (ii) compare the strain value with a predetermined limit associated with successful staple formation, and (iii) generate a signal in response to a comparison between the strain value and the predetermined limit.

Example 2

The apparatus of any one or more of the preceding Examples, wherein the strain measuring assembly comprises a strain gauge attached to a top surface of the first elongate member.

Example 3

The apparatus of any one or more of the preceding Examples, wherein the strain measuring assembly comprises a control unit in communication with the strain gauge.

Example 4

The apparatus of any one or more of the preceding Examples, wherein the strain measuring assembly comprises a battery configured to power both the strain gauge and the control unit.

Example 5

The apparatus of any one or more of the preceding Examples, further comprising a shroud attached to the first elongate member, wherein the control unit and the battery are housed within an interior defined by the shroud.

Example 6

The apparatus of any one or more of the preceding Examples, wherein the strain measuring assembly further comprises a visual indicator associated with the shroud, wherein the visual indicator is configured to display a first indicator if the strain value is outside the predetermined lime, wherein the visual indicator is configured display a second indicator if the strain value is within the predetermined limit.

Example 7

The apparatus of any one or more of the preceding Examples, wherein the first elongate member comprises a latching pin, wherein the strain gauge is directly adjacent to the latching pin.

Example 8

The apparatus of any one or more of the preceding Examples, wherein the latch member comprises a jaw defining a slot, wherein the slot is dimensioned to house the latching pin in the latched state.

Example 9

The apparatus of any one or more of the preceding Examples, wherein the strain measuring assembly comprises a control unit comprising a PCB.

Example 10

The apparatus of any one or more of the preceding Examples, wherein the PCB stores the predetermined limit.

Example 11

The apparatus of any one or more of the preceding Examples, wherein the first elongate member comprises an anvil plate.

Example 12

The apparatus of any one or more of the preceding Examples, wherein the second elongated member comprises a cartridge receiving jaw dimensioned to selectively receive a staple cartridge.

Example 13

The apparatus of any one or more of the preceding Examples, further comprising a lockout assembly configured to inhibit actuation of the firing assembly based on the measured strain value.

Example 14

The apparatus of any one or more of the preceding Examples, wherein the lockout assembly comprises a solenoid.

Example 15

The apparatus of any one or more of the preceding Examples, wherein the first elongate member and the second elongate member configured to releasably couple at a proximal end.

Example 16

An apparatus comprising: (a) a first elongate member having a distal portion configured to present a first stapling surface; (b) a second elongate member having a distal portion configured to present a second stapling surface, wherein the first and second elongate members are configured to releasably couple together at their proximal ends to enable the first and second stapling surfaces to cooperate to clamp and staple tissue with a plurality of staples; (c) a clamp member, wherein the clamp member is movable relative to the first and second elongate members from an open position to a closed position to approximate the first and second stapling surfaces for clamping tissue; and (d) a strain measurement assembly configured to measure a strain value associated with the first elongate member and generate a signal indicative of whether a gap distance between the first and second stapling surfaces is within a predetermined range.

Example 17

The apparatus of any one or more of the preceding Examples, wherein the strain measuring assembly comprises a control unit configured to generate the signal.

Example 18

The apparatus of any one or more of the preceding Examples, wherein the strain measuring assembly comprises a battery configured to power the control unit.

Example 19

The apparatus of any one or more of the preceding Examples, wherein the first elongate member comprises an anvil surface defining a plurality of staple forming pockets.

Example 20

A method of determining whether a gap distance between a first and second stapling surface is within a predetermined range, the method comprising: (a) measuring a strain value on a first elongate member while the first elongate member and a second elongated member cooperate to clamp tissue; (b) comparing the measured strain value to a predetermined limit; and (c) generating a comparison signal in response to the comparison of the measured strain value and the predetermined limit.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Stapler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Surgical Stapler," issued Jun. 23, 2020; U.S. Pat. No. 10,898, 187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgical Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022, issued as U.S. Pat. No. 12,016,555 on Jun. 25, 2024; U.S. Pat. No. 11,224,425, entitled "Surgical Linear Cutter Wishbone Separation Mechanism with Detent,"

issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021, issued as U.S. Pat. No. 11,399,827 on Aug. 2, 2022; U.S. patent application Ser. No. 17/489,879, entitled "Lockout Feature for Linear Surgical Stapler Cartridge," filed Sep. 30, 2021, issued as U.S. Pat. No. 11,937,812 on Mar. 26, 2024; U.S. patent application Ser. No. 29/842,580, entitled "Staple Cartridge for Linear Surgical Stapler," filed Jun. 16, 2022; and/or U.S. patent application Ser. No. 29/842,581, entitled "Linear Surgical Stapler," filed Jun. 16, 2022, issued as U.S. Design Pat. No. D1,067,431 on Mar. 18, 2025. The disclosure of each of these references is incorporated by reference herein, in its entirety.

Furthermore, any one or more of the teachings herein may be combined with any one or more of the teachings disclosed in U.S. patent application Ser. No. 18/500,305, entitled "Clamp Force Sensor for Surgical Stapler," filed Nov. 2, 2023, published as U.S. Pat. Pub. No. 2025/0143696 on May 8, 2025, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
   (a) a first elongate body having a distal portion configured to present a first stapling surface, wherein the first elongate body comprises a latching pin;
   (b) a second elongate body having a distal portion configured to present a second stapling surface, wherein the first and second elongate bodies are configured to releasably couple together to enable the first and second stapling surfaces to cooperate to clamp and staple tissue with a plurality of staples;
   (c) a clamp, wherein the clamp is movable relative to the first and second elongate bodies from a first position to a second position to approximate the first and second stapling surfaces for clamping tissue;
   (d) a latch configured to transition from an unlatched state to a latched state to releasably retain the clamp in the second position;
   (e) a firing assembly, wherein the firing assembly is actuatable from a home position to fire the staples into the clamped tissue; and
   (f) a strain measuring assembly associated with the first elongate body, wherein the strain measuring assembly comprises a strain gauge attached to a top surface of the first elongate body, wherein the strain gauge is directly adjacent to the latching pin, wherein the strain measuring assembly is configured to:
      (i) measure a strain value on the first elongate body,
      (ii) compare the strain value with a predetermined limit associated with successful staple formation, and
      (iii) generate a signal in response to a comparison between the strain value and the predetermined limit.

2. The apparatus of claim 1, wherein the strain measuring assembly comprises a control unit in communication with the strain gauge.

3. The apparatus of claim 2, wherein the strain measuring assembly comprises a battery configured to power both the strain gauge and the control unit.

4. The apparatus of claim 3, further comprising a shroud attached to the first elongate body, wherein the control unit and the battery are housed within an interior defined by the shroud.

5. The apparatus of claim 4, wherein the strain measuring assembly further comprises a visual indicator associated with the shroud, wherein the visual indicator is configured to display a first indicator if the strain value is outside the predetermined lime, wherein the visual indicator is configured display a second indicator if the strain value is within the predetermined limit.

6. The apparatus of claim 1, wherein the latch comprises a jaw defining a slot, wherein the slot is dimensioned to house the latching pin in the latched state.

7. The apparatus of claim 1, wherein the strain measuring assembly comprises a control unit comprising a PCB.

8. The apparatus of claim 7, wherein the PCB stores the predetermined limit.

9. The apparatus of claim 1, wherein the first elongate body comprises an anvil plate.

10. The apparatus of claim 9, wherein the second elongated body comprises a cartridge receiving jaw dimensioned to selectively receive a staple cartridge.

11. The apparatus of claim 1, further comprising a lockout assembly configured to inhibit actuation of the firing assembly based on the measured strain value.

12. The apparatus of claim 11, wherein the lockout assembly comprises a solenoid.

13. The apparatus of claim 1, wherein the first elongate body and the second elongate body configured to releasably couple at a proximal end.

14. An apparatus comprising:
   (a) a first elongate body having a distal portion configured to present a first stapling surface, wherein the first elongate body comprises a latching pin;
   (b) a second elongate body having a distal portion configured to present a second stapling surface, wherein the first and second elongate bodies are configured to releasably couple together at their proximal ends to enable the first and second stapling surfaces to cooperate to clamp and staple tissue with a plurality of staples;
   (c) a clamp, wherein the clamp is movable relative to the first and second elongate bodies from an open position to a closed position to approximate the first and second stapling surfaces for clamping tissue; and
   (d) a strain measurement assembly configured to measure a strain value associated with the first elongate body and generate a signal indicative of whether a gap distance between the first and second stapling surfaces is within a predetermined range, wherein the strain measurement assembly comprises a strain gauge attached to a top surface of the first elongate body, wherein a longitudinal axis through the latching pin intersects with an axis normal to the top surface of the first elongate body, and the axis normal to the top surface of the first elongate body intersects the strain measurement assembly.

15. The apparatus of claim 14, wherein the strain measuring assembly comprises a control unit configured to generate the signal.

16. The apparatus of claim 15, wherein the strain measuring assembly comprises a battery configured to power the control unit.

17. The apparatus of claim 14, wherein the first elongate body comprises an anvil surface defining a plurality of staple forming pockets.

18. A method of determining whether a gap distance between a first and second stapling surface of an apparatus is within a predetermined range, the method comprising:
   (a) measuring a strain value on a first elongate body while the first elongate body and a second elongate body cooperate to clamp tissue;

(b) comparing the measured strain value to a predeter-
mined limit;

(c) generating a comparison signal in response to the
comparison of the measured strain value and the pre-
determined limit; and (d) based on the comparison signal, activating a solenoid
of a lockout assembly of the apparatus to inhibit
actuation of an elongate beam of a firing assembly of
the apparatus.

* * * * *